United States Patent [19]

Scott et al.

[11] Patent Number: 5,741,890
[45] Date of Patent: Apr. 21, 1998

[54] PROTEIN BINDING FRAGMENTS OF GRAVIN

[75] Inventors: John D. Scott; J. Brian Nauert; Theresa M. Klauck, all of Portland, Oreg.

[73] Assignee: Oregon Health Sciences University, Portland, Oreg.

[21] Appl. No.: 769,309

[22] Filed: Dec. 19, 1996

[51] Int. Cl.$^6$ .................................................. C07K 14/00
[52] U.S. Cl. ........................ 530/300; 530/324; 530/350; 435/691
[58] Field of Search ............................ 530/350, 300, 530/324; 435/69.1

[56] References Cited

U.S. PATENT DOCUMENTS

| | | | |
|---|---|---|---|
| 4,766,046 | 8/1988 | Abra et al. | 424/450 |
| 5,169,637 | 12/1992 | Lenk et al. | 424/450 |
| 5,180,713 | 1/1993 | Abra et al. | 514/31 |
| 5,185,154 | 2/1993 | Lasic et al. | 424/450 |
| 5,204,112 | 4/1993 | Hope et al. | 424/450 |
| 5,252,263 | 10/1993 | Hope et al. | 264/4.3 |

FOREIGN PATENT DOCUMENTS

WO 92/02244   2/1992   WIPO.

OTHER PUBLICATIONS

Aderem, A., "The MARCKS Brothers: A Family of Protein Kinase C Substrates," *Cell*, 71:713–716 (1992).
Cappecchi, M., "Altering the Genome by Homologous Recombination," *Science*, 244:1288–1292 (1989).
Carr et al., "Interaction of the Regulatory Subunit (RII) of cAMP–dependent Protein Kinase with RII–anchoring Proteins Occurs Through an Amphipathic Helix Binding Motif," *J. Biol. Chem.*, 266:14188–14192 (1991).
Carr et al., "Association of the Type II cAMP–dependent Protein Kinase with a Human Thyroid RII–anchoring Protein," *J. Biol. Chem.*, 267:13376–13382 (1992).
Chapline et al., "Interaction Cloning of Protein Kinase C Substrates," *J. Biol. Chem.*, 268:6858–6861 (1993).
Chapline et al., "Identification of a Major Protein Kinase C–binding Protein and Substrate in Rat Embryo Fibroblasts," *J. Biol. Chem.*, 271:6417–6422 (1996).
Cheley et al., "Type II Regulatory Subunits of cAMP–dependent Protein Kinase and Their Binding Proteins in the Nervous System of *Aplysia californica*," *J. Biol. Chem.*, 269:2911–2920 (1994).
Chen et al., "Molecular Cloning of cDNA Encoding the 110 kDa and 21 kDa Regulatory Subunits of Smooth Muscle Protein Phosphatase 1M," *FEBS Letters*, 356:51–55 (1994).
Choi et al., "Ste5 Tethers Multiple Protein Kinases in the MAP Kinase Cascade Required for Mating in *S. cerevisiae*," *Cell*, 78:499–512 (1994).
Coghlan et al., "Cloning and Characterization of AKAP 95, a Nuclear Protein that Associates with the Regulatory Subunit of Type II cAMP–dependent Protein Kinase," *J. Biol. Chem.*, 269:7658–7665 (1994).

Coghlan et al., "A Targeting Model for Reversible Phosphorylation," *Advances in Protein Phosphatases*, 9:51–61 (1995a).
Coghlan et al., "Association of Protein Kinase A and Protein Phosphatase 2B with a Common Anchoring Protein," *Science*, 267:108–111 (1995b).
Csortos et al., "High Complexity in the Expression of the B' Subunit of Protein Phosphatase $2A_0$," *J. Biol. Chem.*, 271:2578–2588 (1966).
Davies et al., "The Resonant Mirror: A Versatile Tool for the Study of Biomolecular Interactions," *Techniques in Protein Chemistry*, 5:285–292 (1994).
De Camilli et al., Heterogenous Distribution of the cAMP Receptor Protein RII in the Nervous System: Evidence for its Intracellular Accumulation on Microtubules, Microtubule–organizing Centers, and in the Area of the Golgi Complex, *J. Cell Biol.*, 103:189–203 (1986).
Eichholtz et al., "A Myristoylated Pseudosubstrate Peptide, a Novel Protein Kinase C Inhibitor," *J. Biol. Chem.*, 268:1982–1986 (1993).
Faux and Scott, "Molecular Glue: Kinase Anchoring and Scaffold Proteins," *Cell*, 85:9–12 (1996a).
Faux and Scott, "More on Target with Protein Phosphorylation: Conferring Specificity by Location," *TIBS*, 21:312–315 (1996b).
Gill, G.N., "The Enigma of LIM Domains," *Structure*, 3:1285–1289 (1995).
Gluck and Ben-Ze'ev, "Modulation of α–actinin Levels Affects Cell Motility and Confers Tumorigenicity on 3T3 Cells," *J. Cell Science*, 107:1773–1782 (1994).
Gordon et al., "Molecular Cloning and Preliminary Characterization of a Novel Cytoplasmic Antigen Recognized by Myasthenia Gravis Sera," *J. Clin. Invest.*, 90:992–999 (1992).
Grove et al., "Restricted Endothelial Cell Expression of Gravin In Vivo," *Anat. Rec.*, 239:231–242 (1994).
Herskowitz, "MAP Kinase Pathways in Yeast: For Mating and More." *Cell*, 80:187–197 (1995).
Hibbs et al., "The Cytoplasmic Domain of the Integrin Lymphocyte Function–associated Antigen 1 β Subunit: Sites Required for Binding to Intercellular Adhesion Molecule 1 and the Phorbol Ester–stimulated Phosphorylation Site," *J. Exp. Med.*, 174:1227–1238 (1991).
Hunter, T., "Protein Kinases and Phosphatases: The Yin and Yang of Protein Phosphorylation and Signaling," *Cell*, 80:225–236 (1995).

(List continued on next page.)

*Primary Examiner*—Sally P. Teng
*Attorney, Agent, or Firm*—Marshall, O'Toole, Gerstein, Murray & Borun

[57] ABSTRACT

The present invention generally relates to protein binding fragments of gravin and polynucleotides encoding these fragments. The protein binding fragments include fragments which bind to the Type II regulatory subunit of cAMP–dependent protein kinase or protein kinase C. This invention further provides antibodies to the protein binding fragments and assays for identifying compounds which modulate the binding of gravin to the binding protein.

3 Claims, 2 Drawing Sheets

OTHER PUBLICATIONS

Klauck et al., "Coordination of Three Signaling Enzymes by AKAP79, a Mammalian Scaffold Protein," *Science*, 271:1589–1592 (1996).

Liao et al., "Protein Kinase C Domains Involved in Interactions with Other Proteins," *Biochem.*, 33:1229–1233 (1994).

Lin et al., "A Novel src–and ras–suppressed Protein Kinase C Substrate Associated with Cytoskeletal Architecture," *J. Biol. Chem.*, 271:28430–28438 (1996).

Lin et al., "Isolation and Characterization of a Novel Mitogenic Regulatory Gene, 322, Which is Transcriptionally Suppressed in Cells Transformed by src and ras," *Mol. Cell Biol.*, 15:2754–2762 (1995).

Lohman, et al., "High–affinity Binding of the Regulatory Subunit ($R_{II}$) of cAMP–dependent Protein Kinase to Microtubule–associated and other Cellular Proteins," *Proc. Nat. Acad. Sci.*, 81:6723–6727 (1984).

Mochly–Rosen, D., "Localization of Protein Kinases by Anchoring Proteins: A Theme in Signal Transduction," *Science*, 268:247–251 (1995).

Mochly–Rosen et al., "Identification of Intracellular Receptor Proteins for Activated Protein Kinase C," *Proc. Natl. Acad. Sci. U.S.A.*, 88:3997–4000 (1991).

Newton, A.C., "Seeing Two Domains," *Current Biology*, 5:973–976 (1995).

Newton, A.C., "Protein Kinase C: Ports of Anchor in the Cell," *Current Biology*, 6:806–809 (1996).

Orr et al., "Requirement for Negative Charge on Activation Loop of Protein Kinase C," *J. Biol. Chem.*, 269:27715–27718 (1994).

Papayannopoulou et al., "Human Erythroleukemia Cell Line (HEL) Undergoes a Drastic Macrophage–Like Shift with TPA," *Blood*, 62:832–845 (1983).

Rosenmund et al., "Anchoring of Protein Kinase A is Required for Modulation of AMPA/kainate Receptors on Hippocampal Neurons," *Nature*, 368:853–856 (1994).

Rubino et al., "Localization and Characterization of the Binding Site for the Regulatory Subunit of Type II cAMP–Dependent Protein Kinase on MAP2," *Neuron*, 3:631–638 (1989).

Sambrook et al., 9.47–9.51 in vol. II Molecular Cloning, Cold Spring Harbor Laboratory Press, Cold Spring Harbor, New York (1989).

Scott and McCartney, "Localization of A–Kinase through Anchoring Proteins," *Molecular Endocrinology*, 8:5–11 (1994).

Scott et al., "The Molecular Cloning of a Type II Regulatory Subunit of the cAMP–dependent Protein Kinase from Rat Skeletal Muscle and Mouse Brain," *Pro. Nat. Acad. Sci. U.S.A.*, 84:5192–5196 (1987).

Shibasaki et al., "Role of Kinases and the Phosphatase Calcineurin in the Nuclear Shuttling of Transcription Factor NF–AT4," *Nature*, 382:370–373 (1996).

Staudinger et al., "PCK1: A Perinuclear Binding Protein and Substrate for Protein Kinase C Isolated by the Yeast Two–hybrid System," *J. Cell. Biol.*, 128:263–271 (1995).

Stewart and Young, *Solid Phase Peptide Synthesis*, 2nd Ed., Pierce Chemical Company (1984).

Tam et al., "$S_N2$ Deprotection of Synthetic Peptides with a Low Concentration of HF in Dimethyl Sulfide: Evidence and Application in Peptide Synthesis," *J. Am. Chem. Soc.*, 105:6442–6455 (1983).

Theurkauf et al., "Molecular Characterization of the cAMP–dependent Protein Kinase Bound to Microtubule–associated Protein 2," *J. Biol. Chem.*, 257:3284–3290 (1982).

Valmu et al., "Treatment with Okadaic Acid Reveals Strong Threonine Phosphorylation of CD18 after Activation of CD11/CD18 Leukocyte Integrins with Phorbol Esters or CD3 Antibodies," *J. Immunol.*, 155:1175–1183 (1995).

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 57 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Val Ala Ile Glu Asp Leu Glu Pro Glu Asn Gly Ile Leu Glu Leu Glu
1               5                   10                  15

Thr Lys Ser Ser Lys Leu Val Gln Asn Ile Ile Gln Thr Ala Val Asp
            20                  25                  30

Gln Phe Val Arg Thr Glu Glu Thr Ala Thr Glu Met Leu Thr Ser Glu
        35                  40                  45

Leu Gln Thr Gln Ala His Val Ile Lys
50                  55
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Ile Leu Glu Leu Glu Thr Lys Ser Ser Lys Leu Val Gln Asn Ile Ile
1               5                   10                  15

Gln Thr Ala Val Asp Gln Phe Val Arg Thr Glu
            20                  25
```

( 2 ) INFORMATION FOR SEQ ID NO:3:

( i ) SEQUENCE CHARACTERISTICS:
        ( A ) LENGTH: 292 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Lys Glu Glu Gly Glu Glu Lys Gln Glu Lys Glu Pro Ser Lys Ser Ala
1               5                   10                  15

Glu Ser Pro Thr Ser Pro Val Thr Ser Glu Thr Gly Ser Thr Phe Lys
            20                  25                  30

Lys Phe Phe Thr Gln Gly Trp Ala Gly Trp Arg Lys Lys Thr Ser Phe
        35                  40                  45

Arg Lys Pro Lys Glu Asp Glu Val Glu Ala Ser Glu Lys Lys Lys Glu
    50                  55                  60

Gln Glu Pro Glu Lys Val Asp Thr Glu Glu Asp Gly Lys Ala Glu Val
65                  70                  75                  80

Ala Ser Glu Lys Leu Thr Ala Ser Glu Gln Ala His Pro Gln Glu Pro
            85                  90                  95

Ala Glu Ser Ala His Glu Pro Arg Leu Ser Ala Glu Tyr Glu Lys Val
        100                 105                 110

Glu Leu Pro Ser Glu Glu Gln Val Ser Gly Ser Gln Gly Pro Ser Glu
```

|     | 115 |     |     |     |     | 120 |     |     |     |     | 125 |     |     |     |
|-----|-----|-----|-----|-----|-----|-----|-----|-----|-----|-----|-----|-----|-----|-----|
| Glu | Lys<br>130 | Pro | Ala | Pro | Leu | Ala<br>135 | Thr | Glu | Val | Phe | Asp<br>140 | Glu | Lys | Ile | Glu |
| Val<br>145 | His | Gln | Glu | Glu | Val<br>150 | Val | Ala | Glu | Val | His<br>155 | Val | Ser | Thr | Val | Glu<br>160 |
| Glu | Arg | Thr | Glu | Glu<br>165 | Gln | Lys | Thr | Glu | Val<br>170 | Glu | Glu | Thr | Ala | Gly<br>175 | Ser |
| Val | Pro | Ala | Glu<br>180 | Glu | Leu | Val | Gly | Met<br>185 | Asp | Ala | Glu | Pro | Gln<br>190 | Glu | Ala |
| Glu | Pro | Ala<br>195 | Lys | Glu | Leu | Val | Lys<br>200 | Leu | Lys | Glu | Thr | Cys<br>205 | Val | Ser | Gly |
| Glu | Asp<br>210 | Pro | Thr | Gln | Gly | Ala<br>215 | Asp | Leu | Ser | Pro | Asp<br>220 | Glu | Lys | Val | Leu |
| Ser<br>225 | Lys | Pro | Pro | Glu | Gly<br>230 | Val | Val | Ser | Glu | Val<br>235 | Glu | Met | Leu | Ser | Ser<br>240 |
| Gln | Glu | Arg | Met | Lys<br>245 | Val | Gln | Gly | Ser | Pro<br>250 | Leu | Lys | Lys | Leu | Phe<br>255 | Thr |
| Ser | Thr | Gly | Leu<br>260 | Lys | Lys | Leu | Ser | Gly<br>265 | Lys | Lys | Gln | Lys | Gly<br>270 | Lys | Arg |
| Gly | Gly | Gly<br>275 | Asp | Glu | Glu | Ser | Gly<br>280 | Glu | His | Thr | Gln | Val<br>285 | Pro | Ala | Asp |
| Ser | Pro | Asp<br>290 | Ser |     |     |     |     |     |     |     |     |     |     |     |     |

( 2 ) INFORMATION FOR SEQ ID NO:4:

( i ) SEQUENCE CHARACTERISTICS:
        ( A ) LENGTH: 6605 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 192..5531

( x i ) SEQUENCE DESCRIPTION: SEQ ID NO:4:

```
CCTTCTTTTA AGGAGTTTGC CGCGAGCGCG TCTCCTTCAT TCGCAGGCTG GGCGCGTTCG        60

CAGTCGGCTG GCGGCGAAGG AAGGCGCTCT CGGGACCTCA CGGGCGCGCG TCTTTTGGCT       120

CTTGCCCCTG TCCCTGCGGC TTGGGGAAAG CGTAACCCGG CGGCTAGGCG CGGGAGAAGT       180

GCGGAGGAGC C ATG GGC GCC GGG AGC TCC ACC GAG CAG CGC AGC CCG GAG       230
             Met Gly Ala Gly Ser Ser Thr Glu Gln Arg Ser Pro Glu
               1               5                  10

CAG CCG CCC GAG GGG AGC TCC ACG CCG GCT GAG CCC GAG CCC AGC GGC       278
Gln Pro Pro Glu Gly Ser Ser Thr Pro Ala Glu Pro Glu Pro Ser Gly
         15                  20                  25

GGC GGC CCC TCG GCC GAG GCG GCG CCA GAC ACC ACC GCG GAC CCC GCC       326
Gly Gly Pro Ser Ala Glu Ala Ala Pro Asp Thr Thr Ala Asp Pro Ala
 30                  35                  40                  45

ATC GCT GCC TCG GAC CCC GCC ACC AAG CTC CTA CAG AAG AAT GGT CAG       374
Ile Ala Ala Ser Asp Pro Ala Thr Lys Leu Leu Gln Lys Asn Gly Gln
                 50                  55                  60

CTG TCC ACC ATC AAT GGC GTA GCT GAG CAA GAT GAG CTC AGC CTC CAG       422
Leu Ser Thr Ile Asn Gly Val Ala Glu Gln Asp Glu Leu Ser Leu Gln
             65                  70                  75

GAG GGT GAC CTA AAT GGC CAG AAA GGA GCC TTG AAC GGT CAA GGA GCC       470
Glu Gly Asp Leu Asn Gly Gln Lys Gly Ala Leu Asn Gly Gln Gly Ala
```

-continued

|  |  | 80 |  |  |  |  | 85 |  |  |  |  | 90 |  |  |  |  |
|---|---|---|---|---|---|---|---|---|---|---|---|---|---|---|---|---|
| CTA | AAC | AGC | CAG | GAG | GAA | GAA | GAA | GTC | ATT | GTC | ACG | GAG | GTT | GGA | CAG | 518 |
| Leu | Asn | Ser | Gln | Glu | Glu | Glu | Glu | Val | Ile | Val | Thr | Glu | Val | Gly | Gln |  |
|  | 95 |  |  |  | 100 |  |  |  |  | 105 |  |  |  |  |  |  |
| AGA | GAC | TCT | GAA | GAT | GTG | AGC | GAA | AGA | GAC | TCC | GAT | AAA | GAG | ATG | GCT | 566 |
| Arg | Asp | Ser | Glu | Asp | Val | Ser | Glu | Arg | Asp | Ser | Asp | Lys | Glu | Met | Ala |  |
| 110 |  |  |  |  | 115 |  |  |  |  | 120 |  |  |  |  | 125 |  |
| ACT | AAG | TCA | GCG | GTT | GTT | CAC | GAC | ATC | ACA | GAT | GAT | GGG | CAG | GAG | GAG | 614 |
| Thr | Lys | Ser | Ala | Val | Val | His | Asp | Ile | Thr | Asp | Asp | Gly | Gln | Glu | Glu |  |
|  |  |  |  | 130 |  |  |  |  | 135 |  |  |  |  | 140 |  |  |
| AAC | CGA | AAT | ATC | GAA | CAG | ATT | CCT | TCT | TCA | GAA | AGC | AAT | TTA | GAA | GAG | 662 |
| Asn | Arg | Asn | Ile | Glu | Gln | Ile | Pro | Ser | Ser | Glu | Ser | Asn | Leu | Glu | Glu |  |
|  |  |  | 145 |  |  |  |  |  | 150 |  |  |  |  | 155 |  |  |
| CTA | ACA | CAA | CCC | ACT | GAG | TCC | CAG | GCT | AAT | GAT | ATT | GGA | TTT | AAG | AAG | 710 |
| Leu | Thr | Gln | Pro | Thr | Glu | Ser | Gln | Ala | Asn | Asp | Ile | Gly | Phe | Lys | Lys |  |
|  |  | 160 |  |  |  |  | 165 |  |  |  |  | 170 |  |  |  |  |
| GTG | TTT | AAG | TTT | GTT | GGC | TTT | AAA | TTC | ACT | GTG | AAA | AAG | GAT | AAG | ACA | 758 |
| Val | Phe | Lys | Phe | Val | Gly | Phe | Lys | Phe | Thr | Val | Lys | Lys | Asp | Lys | Thr |  |
| 175 |  |  |  |  | 180 |  |  |  |  | 185 |  |  |  |  |  |  |
| GAG | AAG | CCT | GAC | ACT | GTC | CAG | CTA | CTC | ACT | GTG | AAG | AAA | GAT | GAA | GGG | 806 |
| Glu | Lys | Pro | Asp | Thr | Val | Gln | Leu | Leu | Thr | Val | Lys | Lys | Asp | Glu | Gly |  |
| 190 |  |  |  |  | 195 |  |  |  |  | 200 |  |  |  |  | 205 |  |
| GAG | GGA | GCA | GCA | GGG | GCT | GGC | GAC | CAC | CAG | GAC | CCC | AGC | CTT | GGG | GCT | 854 |
| Glu | Gly | Ala | Ala | Gly | Ala | Gly | Asp | His | Gln | Asp | Pro | Ser | Leu | Gly | Ala |  |
|  |  |  |  | 210 |  |  |  |  | 215 |  |  |  |  | 220 |  |  |
| GGA | GAA | GCA | GCA | TCC | AAA | GAA | AGC | GAA | CCC | AAA | CAA | TCT | ACA | GAG | AAA | 902 |
| Gly | Glu | Ala | Ala | Ser | Lys | Glu | Ser | Glu | Pro | Lys | Gln | Ser | Thr | Glu | Lys |  |
|  |  |  | 225 |  |  |  |  |  | 230 |  |  |  |  | 235 |  |  |
| CCC | GAA | GAG | ACC | CTG | AAG | CGT | GAG | CAA | AGC | CAC | GCA | GAA | ATT | TCT | CCC | 950 |
| Pro | Glu | Glu | Thr | Leu | Lys | Arg | Glu | Gln | Ser | His | Ala | Glu | Ile | Ser | Pro |  |
|  |  | 240 |  |  |  |  | 245 |  |  |  |  | 250 |  |  |  |  |
| CCA | GCC | GAA | TCT | GGC | CAA | GCA | GTG | GAG | GAA | TGC | AAA | GAG | GAA | GGA | GAA | 998 |
| Pro | Ala | Glu | Ser | Gly | Gln | Ala | Val | Glu | Glu | Cys | Lys | Glu | Glu | Gly | Glu |  |
| 255 |  |  |  |  | 260 |  |  |  |  | 265 |  |  |  |  |  |  |
| GAG | AAA | CAA | GAA | AAA | GAA | CCT | AGC | AAG | TCT | GCA | GAA | TCT | CCG | ACT | AGT | 1046 |
| Glu | Lys | Gln | Glu | Lys | Glu | Pro | Ser | Lys | Ser | Ala | Glu | Ser | Pro | Thr | Ser |  |
| 270 |  |  |  |  | 275 |  |  |  |  | 280 |  |  |  |  | 285 |  |
| CCC | GTG | ACC | AGT | GAA | ACA | GGA | TCA | ACC | TTC | AAA | AAA | TTC | TTC | ACT | CAA | 1094 |
| Pro | Val | Thr | Ser | Glu | Thr | Gly | Ser | Thr | Phe | Lys | Lys | Phe | Phe | Thr | Gln |  |
|  |  |  |  | 290 |  |  |  |  | 295 |  |  |  |  | 300 |  |  |
| GGT | TGG | GCC | GGC | TGG | CGC | AAA | AAG | ACC | AGT | TTC | AGG | AAG | CCG | AAG | GAG | 1142 |
| Gly | Trp | Ala | Gly | Trp | Arg | Lys | Lys | Thr | Ser | Phe | Arg | Lys | Pro | Lys | Glu |  |
|  |  |  | 305 |  |  |  |  |  | 310 |  |  |  |  | 315 |  |  |
| GAT | GAA | GTG | GAA | GCT | TCA | GAG | AAG | AAA | AAG | GAA | CAA | GAG | CCA | GAA | AAA | 1190 |
| Asp | Glu | Val | Glu | Ala | Ser | Glu | Lys | Lys | Lys | Glu | Gln | Glu | Pro | Glu | Lys |  |
|  |  | 320 |  |  |  |  | 325 |  |  |  |  | 330 |  |  |  |  |
| GTA | GAC | ACA | GAA | GAA | GAC | GGA | AAG | GCA | GAG | GTT | GCC | TCC | GAG | AAA | CTG | 1238 |
| Val | Asp | Thr | Glu | Glu | Asp | Gly | Lys | Ala | Glu | Val | Ala | Ser | Glu | Lys | Leu |  |
|  | 335 |  |  |  |  | 340 |  |  |  |  | 345 |  |  |  |  |  |
| ACC | GCC | TCC | GAG | CAA | GCC | CAC | CCA | CAG | GAG | CCG | GCA | GAA | AGT | GCC | CAC | 1286 |
| Thr | Ala | Ser | Glu | Gln | Ala | His | Pro | Gln | Glu | Pro | Ala | Glu | Ser | Ala | His |  |
| 350 |  |  |  |  | 355 |  |  |  |  | 360 |  |  |  |  | 365 |  |
| GAG | CCC | CGG | TTA | TCA | GCT | GAA | TAT | GAG | AAA | GTT | GAG | CTG | CCC | TCA | GAG | 1334 |
| Glu | Pro | Arg | Leu | Ser | Ala | Glu | Tyr | Glu | Lys | Val | Glu | Leu | Pro | Ser | Glu |  |
|  |  |  | 370 |  |  |  |  | 375 |  |  |  |  | 380 |  |  |  |
| GAG | CAA | GTC | AGT | GGC | TCG | CAG | GGA | CCT | TCT | GAA | GAG | AAA | CCT | GCT | CCG | 1382 |
| Glu | Gln | Val | Ser | Gly | Ser | Gln | Gly | Pro | Ser | Glu | Glu | Lys | Pro | Ala | Pro |  |
|  |  |  | 385 |  |  |  |  | 390 |  |  |  |  | 395 |  |  |  |
| TTG | GCG | ACA | GAA | GTG | TTT | GAT | GAG | AAA | ATA | GAA | GTC | CAC | CAA | GAA | GAG | 1430 |
| Leu | Ala | Thr | Glu | Val | Phe | Asp | Glu | Lys | Ile | Glu | Val | His | Gln | Glu | Glu |  |

|  |  |  |  |  |  |  |  |  |  |  |  |  |  |  |  |  |
|---|---|---|---|---|---|---|---|---|---|---|---|---|---|---|---|---|
|  |  |  |  | 400 |  |  |  |  | 405 |  |  |  |  | 410 |  |  |
| GTT | GTG | GCC | GAA | GTC | CAC | GTC | AGC | ACC | GTG | GAG | GAG | AGA | ACC | GAA | GAG | 1478 |
| Val | Val | Ala | Glu | Val | His | Val | Ser | Thr | Val | Glu | Glu | Arg | Thr | Glu | Glu |  |
|  |  | 415 |  |  |  | 420 |  |  |  | 425 |  |  |  |  |  |  |
| CAG | AAA | ACG | GAG | GTG | GAA | GAA | ACA | GCA | GGG | TCT | GTG | CCA | GCT | GAA | GAA | 1526 |
| Gln | Lys | Thr | Glu | Val | Glu | Glu | Thr | Ala | Gly | Ser | Val | Pro | Ala | Glu | Glu |  |
| 430 |  |  |  | 435 |  |  |  |  | 440 |  |  |  |  |  | 445 |  |
| TTG | GTT | GGA | ATG | GAT | GCA | GAA | CCT | CAG | GAA | GCC | GAA | CCT | GCC | AAG | GAG | 1574 |
| Leu | Val | Gly | Met | Asp | Ala | Glu | Pro | Gln | Glu | Ala | Glu | Pro | Ala | Lys | Glu |  |
|  |  |  |  | 450 |  |  |  |  | 455 |  |  |  |  | 460 |  |  |
| CTG | GTG | AAG | CTC | AAA | GAA | ACG | TGT | GTT | TCC | GGA | GAG | GAC | CCT | ACA | CAG | 1622 |
| Leu | Val | Lys | Leu | Lys | Glu | Thr | Cys | Val | Ser | Gly | Glu | Asp | Pro | Thr | Gln |  |
|  |  |  | 465 |  |  |  |  | 470 |  |  |  |  | 475 |  |  |  |
| GGA | GCT | GAC | CTC | AGT | CCT | GAT | GAG | AAG | GTG | CTG | TCC | AAA | CCC | CCC | GAA | 1670 |
| Gly | Ala | Asp | Leu | Ser | Pro | Asp | Glu | Lys | Val | Leu | Ser | Lys | Pro | Pro | Glu |  |
|  |  | 480 |  |  |  |  | 485 |  |  |  |  | 490 |  |  |  |  |
| GGC | GTT | GTG | AGT | GAG | GTG | GAA | ATG | CTG | TCA | TCA | CAG | GAG | AGA | ATG | AAG | 1718 |
| Gly | Val | Val | Ser | Glu | Val | Glu | Met | Leu | Ser | Ser | Gln | Glu | Arg | Met | Lys |  |
|  | 495 |  |  |  |  | 500 |  |  |  |  | 505 |  |  |  |  |  |
| GTG | CAG | GGA | AGT | CCA | CTA | AAG | AAG | CTT | TTT | ACC | AGC | ACT | GGC | TTA | AAA | 1766 |
| Val | Gln | Gly | Ser | Pro | Leu | Lys | Lys | Leu | Phe | Thr | Ser | Thr | Gly | Leu | Lys |  |
| 510 |  |  |  |  | 515 |  |  |  | 520 |  |  |  |  |  | 525 |  |
| AAG | CTT | TCT | GGA | AAG | AAA | CAG | AAA | GGG | AAA | AGA | GGA | GGA | GGA | GAC | GAG | 1814 |
| Lys | Leu | Ser | Gly | Lys | Lys | Gln | Lys | Gly | Lys | Arg | Gly | Gly | Gly | Asp | Glu |  |
|  |  |  | 530 |  |  |  |  |  | 535 |  |  |  |  | 540 |  |  |
| GAA | TCA | GGG | GAG | CAC | ACT | CAG | GTT | CCA | GCC | GAT | TCT | CCG | GAC | AGC | CAG | 1862 |
| Glu | Ser | Gly | Glu | His | Thr | Gln | Val | Pro | Ala | Asp | Ser | Pro | Asp | Ser | Gln |  |
|  |  | 545 |  |  |  |  | 550 |  |  |  |  | 555 |  |  |  |  |
| GAG | GAG | CAA | AAG | GGC | GAG | AGC | TCT | GCC | TCA | TCC | CCT | GAG | GAG | CCC | GAG | 1910 |
| Glu | Glu | Gln | Lys | Gly | Glu | Ser | Ser | Ala | Ser | Ser | Pro | Glu | Glu | Pro | Glu |  |
|  |  | 560 |  |  |  |  | 565 |  |  |  |  | 570 |  |  |  |  |
| GAG | ATC | ACG | TGT | CTG | GAA | AAG | GGC | TTA | GCC | GAG | GTG | CAG | CAG | GAT | GGG | 1958 |
| Glu | Ile | Thr | Cys | Leu | Glu | Lys | Gly | Leu | Ala | Glu | Val | Gln | Gln | Asp | Gly |  |
|  | 575 |  |  |  |  | 580 |  |  |  |  | 585 |  |  |  |  |  |
| GAA | GCT | GAA | GAA | GGA | GCT | ACT | TCC | GAT | GGA | GAG | AAA | AAA | AGA | GAA | GGT | 2006 |
| Glu | Ala | Glu | Glu | Gly | Ala | Thr | Ser | Asp | Gly | Glu | Lys | Lys | Arg | Glu | Gly |  |
| 590 |  |  |  |  | 595 |  |  |  |  | 600 |  |  |  |  | 605 |  |
| GTC | ACT | CCC | TGG | GCA | TCA | TTC | AAA | AAG | ATG | GTG | ACG | CCC | AAG | AAG | CGT | 2054 |
| Val | Thr | Pro | Trp | Ala | Ser | Phe | Lys | Lys | Met | Val | Thr | Pro | Lys | Lys | Arg |  |
|  |  |  |  | 610 |  |  |  |  | 615 |  |  |  |  |  | 620 |  |
| GTT | AGA | CGG | CCT | TCG | GAA | AGT | GAT | AAA | GAA | GAT | GAG | CTG | GAC | AAG | GTC | 2102 |
| Val | Arg | Arg | Pro | Ser | Glu | Ser | Asp | Lys | Glu | Asp | Glu | Leu | Asp | Lys | Val |  |
|  |  |  | 625 |  |  |  |  | 630 |  |  |  |  | 635 |  |  |  |
| AAG | AGC | GCT | ACC | TTG | TCT | TCC | ACC | GAG | AGC | ACA | GCC | TCT | GAA | ATG | CAA | 2150 |
| Lys | Ser | Ala | Thr | Leu | Ser | Ser | Thr | Glu | Ser | Thr | Ala | Ser | Glu | Met | Gln |  |
|  |  | 640 |  |  |  |  | 645 |  |  |  |  | 650 |  |  |  |  |
| GAA | GAA | ATG | AAA | GGG | AGC | GTG | GAA | GAG | CCA | AAG | CCG | GAA | GAA | CCA | AAG | 2198 |
| Glu | Glu | Met | Lys | Gly | Ser | Val | Glu | Glu | Pro | Lys | Pro | Glu | Glu | Pro | Lys |  |
|  | 655 |  |  |  |  | 660 |  |  |  |  | 665 |  |  |  |  |  |
| CGC | AAG | GTG | GAT | ACC | TCA | GTA | TCT | TGG | GAA | GCT | TTA | ATT | TGT | GTG | GGA | 2246 |
| Arg | Lys | Val | Asp | Thr | Ser | Val | Ser | Trp | Glu | Ala | Leu | Ile | Cys | Val | Gly |  |
| 670 |  |  |  |  | 675 |  |  |  |  | 680 |  |  |  |  | 685 |  |
| TCA | TCC | AAG | AAA | AGA | GCA | AGG | AGA | AGG | TCC | TCT | TCT | GAT | GAG | GAA | GGG | 2294 |
| Ser | Ser | Lys | Lys | Arg | Ala | Arg | Arg | Arg | Ser | Ser | Ser | Asp | Glu | Glu | Gly |  |
|  |  |  |  | 690 |  |  |  |  | 695 |  |  |  |  | 700 |  |  |
| GGA | CCA | AAA | GCA | ATG | GGA | GGA | GAC | CAC | CAG | AAA | GCT | GAT | GAG | GCC | GGA | 2342 |
| Gly | Pro | Lys | Ala | Met | Gly | Gly | Asp | His | Gln | Lys | Ala | Asp | Glu | Ala | Gly |  |
|  |  | 705 |  |  |  |  | 710 |  |  |  |  | 715 |  |  |  |  |
| AAA | GAC | AAA | GAG | ACG | GGG | ACA | GAC | GGG | ATC | CTT | GCT | GGT | TCC | CAA | GAA | 2390 |
| Lys | Asp | Lys | Glu | Thr | Gly | Thr | Asp | Gly | Ile | Leu | Ala | Gly | Ser | Gln | Glu |  |

-continued

| | | | | | | | | | | | | | | | | |
|---|---|---|---|---|---|---|---|---|---|---|---|---|---|---|---|---|
| | | 720 | | | | | 725 | | | | | 730 | | | | |
| CAT | GAT | CCA | GGG | CAG | GGA | AGT | TCC | TCC | CCG | GAG | CAA | GCT | GGA | AGC | CCT | 2438 |
| His | Asp | Pro | Gly | Gln | Gly | Ser | Ser | Ser | Pro | Glu | Gln | Ala | Gly | Ser | Pro | |
| | 735 | | | | | 740 | | | | | 745 | | | | | |
| ACC | GAA | GGG | GAG | GGC | GTT | TCC | ACC | TGG | GAG | TCA | TTT | AAA | AGG | TTA | GTC | 2486 |
| Thr | Glu | Gly | Glu | Gly | Val | Ser | Thr | Trp | Glu | Ser | Phe | Lys | Arg | Leu | Val | |
| 750 | | | | | 755 | | | | | 760 | | | | | 765 | |
| ACG | CCA | AGA | AAA | AAA | TCA | AAG | TCC | AAG | CTG | GAA | GAG | AAA | AGC | GAA | GAC | 2534 |
| Thr | Pro | Arg | Lys | Lys | Ser | Lys | Ser | Lys | Leu | Glu | Glu | Lys | Ser | Glu | Asp | |
| | | | | 770 | | | | | 775 | | | | | 780 | | |
| TCC | ATA | GCT | GGG | TCT | GGT | GTA | GAA | CAT | TCC | ACT | CCA | GAC | ACT | GAA | CCC | 2582 |
| Ser | Ile | Ala | Gly | Ser | Gly | Val | Glu | His | Ser | Thr | Pro | Asp | Thr | Glu | Pro | |
| | | | 785 | | | | | 790 | | | | | 795 | | | |
| GGT | AAA | GAA | GAA | TCC | TGG | GTC | TCA | ATC | AAG | AAG | TTT | ATT | CCT | GGA | CGA | 2630 |
| Gly | Lys | Glu | Glu | Ser | Trp | Val | Ser | Ile | Lys | Lys | Phe | Ile | Pro | Gly | Arg | |
| | | 800 | | | | | 805 | | | | | 810 | | | | |
| AGG | AAG | AAA | AGG | CCA | GAT | GGG | AAA | CAA | GAA | CAA | GCC | CCT | GTT | GAA | GAC | 2678 |
| Arg | Lys | Lys | Arg | Pro | Asp | Gly | Lys | Gln | Glu | Gln | Ala | Pro | Val | Glu | Asp | |
| | 815 | | | | | 820 | | | | | 825 | | | | | |
| GCA | GGG | CCA | ACA | GGG | GCC | AAC | GAA | GAT | GAC | TCT | GAT | GTC | CCG | GCC | GTG | 2726 |
| Ala | Gly | Pro | Thr | Gly | Ala | Asn | Glu | Asp | Asp | Ser | Asp | Val | Pro | Ala | Val | |
| 830 | | | | | 835 | | | | | 840 | | | | | 845 | |
| GTC | CCT | CTG | TCT | GAG | TAT | GAT | GCT | GTA | GAA | AGG | GAG | AAA | ATG | GAG | GCA | 2774 |
| Val | Pro | Leu | Ser | Glu | Tyr | Asp | Ala | Val | Glu | Arg | Glu | Lys | Met | Glu | Ala | |
| | | | | 850 | | | | | 855 | | | | | 860 | | |
| CAG | CAA | GCC | CAA | AAA | GGC | GCA | GAG | CAG | CCC | GAG | CAG | AAG | GCA | GCC | ACT | 2822 |
| Gln | Gln | Ala | Gln | Lys | Gly | Ala | Glu | Gln | Pro | Glu | Gln | Lys | Ala | Ala | Thr | |
| | | | 865 | | | | | 870 | | | | | 875 | | | |
| GAG | GTG | TCC | AAG | GAG | CTC | AGC | GAG | AGT | CAG | GTT | CAT | ATG | ATG | GCA | GCA | 2870 |
| Glu | Val | Ser | Lys | Glu | Leu | Ser | Glu | Ser | Gln | Val | His | Met | Met | Ala | Ala | |
| | | 880 | | | | | 885 | | | | | 890 | | | | |
| GCT | GTC | GCT | GAC | GGG | ACG | AGG | GCA | GCT | ACC | ATT | ATT | GAA | GAA | AGG | TCT | 2918 |
| Ala | Val | Ala | Asp | Gly | Thr | Arg | Ala | Ala | Thr | Ile | Ile | Glu | Glu | Arg | Ser | |
| | 895 | | | | | 900 | | | | | 905 | | | | | |
| CCT | TCT | TGG | ATA | TCT | GCT | TCA | GTG | ACA | GAA | CCT | CTT | GAA | CAA | GTA | GAA | 2966 |
| Pro | Ser | Trp | Ile | Ser | Ala | Ser | Val | Thr | Glu | Pro | Leu | Glu | Gln | Val | Glu | |
| 910 | | | | | 915 | | | | | 920 | | | | | 925 | |
| GCT | GAA | GCC | GCA | CTG | TTA | ACT | GAG | GAG | GTA | TTG | GAA | AGA | GAA | GTA | ATT | 3014 |
| Ala | Glu | Ala | Ala | Leu | Leu | Thr | Glu | Glu | Val | Leu | Glu | Arg | Glu | Val | Ile | |
| | | | | 930 | | | | | 935 | | | | | 940 | | |
| GCA | GAA | GAA | GAA | CCC | CCC | ACG | GTT | ACT | GAA | CCT | CTG | CCA | GAG | AAC | AGA | 3062 |
| Ala | Glu | Glu | Glu | Pro | Pro | Thr | Val | Thr | Glu | Pro | Leu | Pro | Glu | Asn | Arg | |
| | | | 945 | | | | | 950 | | | | | 955 | | | |
| GAG | GCC | CGG | GGC | GAC | ACG | GTC | GTT | AGT | GAG | GCG | GAA | TTG | ACC | CCC | GAA | 3110 |
| Glu | Ala | Arg | Gly | Asp | Thr | Val | Val | Ser | Glu | Ala | Glu | Leu | Thr | Pro | Glu | |
| | | 960 | | | | | 965 | | | | | 970 | | | | |
| GCT | GTG | ACA | GCT | GCA | GAA | ACT | GCA | GGG | CCA | TTG | GGT | TCC | GAA | GAA | GGA | 3158 |
| Ala | Val | Thr | Ala | Ala | Glu | Thr | Ala | Gly | Pro | Leu | Gly | Ser | Glu | Glu | Gly | |
| | 975 | | | | | 980 | | | | | 985 | | | | | |
| ACC | GAA | GCA | TCT | GCT | GCT | GAA | GAG | ACC | ACA | GAA | ATG | GTG | TCA | GCA | GTC | 3206 |
| Thr | Glu | Ala | Ser | Ala | Ala | Glu | Glu | Thr | Thr | Glu | Met | Val | Ser | Ala | Val | |
| 990 | | | | | 995 | | | | | 1000 | | | | | 1005 | |
| TCC | CAG | TTA | ACC | GAC | TCC | CCA | GAC | ACC | ACA | GAG | GAG | GCC | ACT | CCG | GTG | 3254 |
| Ser | Gln | Leu | Thr | Asp | Ser | Pro | Asp | Thr | Thr | Glu | Glu | Ala | Thr | Pro | Val | |
| | | | | 1010 | | | | | 1015 | | | | | 1020 | | |
| CAG | GAG | GTG | GAA | GGT | GGC | GTA | CCT | GAC | ATA | GAA | GAG | CAA | GAG | AGG | CGG | 3302 |
| Gln | Glu | Val | Glu | Gly | Gly | Val | Pro | Asp | Ile | Glu | Glu | Gln | Glu | Arg | Arg | |
| | | | 1025 | | | | | 1030 | | | | | 1035 | | | |
| ACT | CAA | GAG | GTC | CTC | CAG | GCA | GTG | GCA | GAA | AAA | GTG | AAA | GAG | GAA | TCC | 3350 |
| Thr | Gln | Glu | Val | Leu | Gln | Ala | Val | Ala | Glu | Lys | Val | Lys | Glu | Glu | Ser | |

-continued

|  |  |  |
|---|---|---|
| 1040 | 1045 | 1050 |

| | | |
|---|---|---|
| CAG CTG CCT GGC ACC GGT GGG CCA GAA GAT GTG CTT CAG CCT GTG CAG<br>Gln Leu Pro Gly Thr Gly Gly Pro Glu Asp Val Leu Gln Pro Val Gln<br>　　1055　　　　　　　　1060　　　　　　　　1065 | 3398 |
| AGA GCA GAG GCA GAA AGA CCA GAA GAG CAG GCT GAA GCG TCG GGT CTG<br>Arg Ala Glu Ala Glu Arg Pro Glu Glu Gln Ala Glu Ala Ser Gly Leu<br>1070　　　　　　　　1075　　　　　　　　1080　　　　　　　　1085 | 3446 |
| AAG AAA GAG ACG GAT GTA GTG TTG AAA GTA GAT GCT CAG GAG GCA AAA<br>Lys Lys Glu Thr Asp Val Val Leu Lys Val Asp Ala Gln Glu Ala Lys<br>　　　　　　　　1090　　　　　　　　1095　　　　　　　　1100 | 3494 |
| ACT GAG CCT TTT ACA CAA GGG AAG GTG GTG GGG CAG ACC ACC CCA GAA<br>Thr Glu Pro Phe Thr Gln Gly Lys Val Val Gly Gln Thr Thr Pro Glu<br>　　　　　　　　1105　　　　　　　　1110　　　　　　　　1115 | 3542 |
| AGC TTT GAA AAA GCT CCT CAA GTC ACA GAG AGC ATA GAG TCC AGT GAG<br>Ser Phe Glu Lys Ala Pro Gln Val Thr Glu Ser Ile Glu Ser Ser Glu<br>　　　　　　　　1120　　　　　　　　1125　　　　　　　　1130 | 3590 |
| CTT GTA ACC ACT TGT CAA GCC GAA ACC TTA GCT GGG GTA AAA TCA CAG<br>Leu Val Thr Thr Cys Gln Ala Glu Thr Leu Ala Gly Val Lys Ser Gln<br>　　　　　　　　1135　　　　　　　　1140　　　　　　　　1145 | 3638 |
| GAG ATG GTG ATG GAA CAG GCT ATC CCC CCT GAC TCG GTG GAA ACC CCT<br>Glu Met Val Met Glu Gln Ala Ile Pro Pro Asp Ser Val Glu Thr Pro<br>1150　　　　　　　　1155　　　　　　　　1160　　　　　　　　1165 | 3686 |
| ACA GAC AGT GAG ACT GAT GGA AGC ACC CCC GTA GCC GAC TTT GAC GCA<br>Thr Asp Ser Glu Thr Asp Gly Ser Thr Pro Val Ala Asp Phe Asp Ala<br>　　　　　　　　1170　　　　　　　　1175　　　　　　　　1180 | 3734 |
| CCA GGC ACA ACC CAG AAA GAC GAG ATT GTG GAA ATC CAT GAG GAG AAT<br>Pro Gly Thr Thr Gln Lys Asp Glu Ile Val Glu Ile His Glu Glu Asn<br>　　　　　　　　1185　　　　　　　　1190　　　　　　　　1195 | 3782 |
| GAG GTG CAT CTG GTA CCA GTC AGG GGC ACA GAA GCA GAG GCA GTT CCT<br>Glu Val His Leu Val Pro Val Arg Gly Thr Glu Ala Glu Ala Val Pro<br>　　　　1200　　　　　　　　1205　　　　　　　　1210 | 3830 |
| GCA CAG AAA GAG AGG CCT CCA GCA CCT TCC AGT TTT GTG TTC CAG GAA<br>Ala Gln Lys Glu Arg Pro Pro Ala Pro Ser Ser Phe Val Phe Gln Glu<br>　　　1215　　　　　　　　1220　　　　　　　　1225 | 3878 |
| GAA ACT AAA GAA CAA TCA AAG ATG GAA GAC ACT CTA GAG CAT ACA GAT<br>Glu Thr Lys Glu Gln Ser Lys Met Glu Asp Thr Leu Glu His Thr Asp<br>1230　　　　　　　　1235　　　　　　　　1240　　　　　　　　1245 | 3926 |
| AAA GAG GTG TCA GTG GAA ACT GTA TCC ATT CTG TCA AAG ACT GAG GGG<br>Lys Glu Val Ser Val Glu Thr Val Ser Ile Leu Ser Lys Thr Glu Gly<br>　　　　　　　　1250　　　　　　　　1255　　　　　　　　1260 | 3974 |
| ACT CAA GAG GCT GAC CAG TAT GCT GAT GAG AAA ACC AAA GAC GTA CCA<br>Thr Gln Glu Ala Asp Gln Tyr Ala Asp Glu Lys Thr Lys Asp Val Pro<br>　　　1265　　　　　　　　1270　　　　　　　　1275 | 4022 |
| TTT TTC GAA GGA CTT GAG GGG TCT ATA GAC ACA GGC ATA ACA GTC AGT<br>Phe Phe Glu Gly Leu Glu Gly Ser Ile Asp Thr Gly Ile Thr Val Ser<br>　　　　1280　　　　　　　　1285　　　　　　　　1290 | 4070 |
| CGG GAA AAG GTC ACT GAA GTT GCC CTT AAA GGT GAA GGG ACA GAA GAA<br>Arg Glu Lys Val Thr Glu Val Ala Leu Lys Gly Glu Gly Thr Glu Glu<br>　　　1295　　　　　　　　1300　　　　　　　　1305 | 4118 |
| GCT GAA TGT AAA AAG GAT GAT GCT CTT GAA CTG CAG AGT CAC GCT AAG<br>Ala Glu Cys Lys Lys Asp Asp Ala Leu Glu Leu Gln Ser His Ala Lys<br>1310　　　　　　　　1315　　　　　　　　1320　　　　　　　　1325 | 4166 |
| TCT CCT CCA TCC CCC GTG GAG AGA GAG ATG GTA GTT CAA GTC GAA AGG<br>Ser Pro Pro Ser Pro Val Glu Arg Glu Met Val Val Gln Val Glu Arg<br>　　　　　　　　1330　　　　　　　　1335　　　　　　　　1340 | 4214 |
| GAG AAA ACA GAA GCA GAG CCA ACC CAT GTG AAT GAA GAG AAG CTT GAG<br>Glu Lys Thr Glu Ala Glu Pro Thr His Val Asn Glu Glu Lys Leu Glu<br>　　　　　　　　1345　　　　　　　　1350　　　　　　　　1355 | 4262 |
| CAC GAA ACA GCT GTT ACC GTA TCT GAA GAG GTC AGT AAG CAG CTC CTC<br>His Glu Thr Ala Val Thr Val Ser Glu Glu Val Ser Lys Gln Leu Leu | 4310 |

```
                    1360                        1365                         1370
CAG  ACA  GTG  AAT  GTG  CCC  ATC  ATA  GAT  GGG  GCA  AAG  GAA  GTC  AGC  AGT     4358
Gln  Thr  Val  Asn  Val  Pro  Ile  Ile  Asp  Gly  Ala  Lys  Glu  Val  Ser  Ser
     1375                      1380                     1385

TTG  GAA  GGA  AGC  CCT  CCT  CCC  TGC  CTA  GGT  CAA  GAG  GAG  GCA  GTA  TGC     4406
Leu  Glu  Gly  Ser  Pro  Pro  Pro  Cys  Leu  Gly  Gln  Glu  Glu  Ala  Val  Cys
1390                     1395                     1400                     1405

ACC  AAA  ATT  CAA  GTT  CAG  AGC  TCT  GAG  GCA  TCA  TTC  ACT  CTA  ACA  GCG     4454
Thr  Lys  Ile  Gln  Val  Gln  Ser  Ser  Glu  Ala  Ser  Phe  Thr  Leu  Thr  Ala
                    1410                     1415                     1420

GCT  GCA  GAG  GAG  GAA  AAG  GTC  TTA  GGA  GAA  ACT  GCC  AAC  ATT  TTA  GAA     4502
Ala  Ala  Glu  Glu  Glu  Lys  Val  Leu  Gly  Glu  Thr  Ala  Asn  Ile  Leu  Glu
               1425                     1430                     1435

ACA  GGT  GAA  ACG  TTG  GAG  CCT  GCA  GGT  GCA  CAT  TTA  GTT  CTG  GAA  GAG     4550
Thr  Gly  Glu  Thr  Leu  Glu  Pro  Ala  Gly  Ala  His  Leu  Val  Leu  Glu  Glu
          1440                     1445                     1450

AAA  TCC  TCT  GAA  AAA  AAT  GAA  GAC  TTT  GCC  GCT  CAT  CCA  GGG  GAA  GAT     4598
Lys  Ser  Ser  Glu  Lys  Asn  Glu  Asp  Phe  Ala  Ala  His  Pro  Gly  Glu  Asp
     1455                     1460                     1465

GCT  GTG  CCC  ACA  GGG  CCC  GAC  TGT  CAG  GCA  AAA  TCG  ACA  CCA  GTG  ATA     4646
Ala  Val  Pro  Thr  Gly  Pro  Asp  Cys  Gln  Ala  Lys  Ser  Thr  Pro  Val  Ile
1470                     1475                     1480                     1485

GTA  TCT  GCT  ACT  ACC  AAG  AAA  GGC  TTA  AGT  TCC  GAC  CTG  GAA  GGA  GAG     4694
Val  Ser  Ala  Thr  Thr  Lys  Lys  Gly  Leu  Ser  Ser  Asp  Leu  Glu  Gly  Glu
                    1490                     1495                     1500

AAA  ACC  ACA  TCA  CTG  AAG  TGG  AAG  TCA  GAT  GAA  GTC  GAT  GAG  CAG  GTT     4742
Lys  Thr  Thr  Ser  Leu  Lys  Trp  Lys  Ser  Asp  Glu  Val  Asp  Glu  Gln  Val
               1505                     1510                     1515

GCT  TGC  CAG  GAG  GTC  AAA  GTG  AGT  GTA  GCA  ATT  GAG  GAT  TTA  GAG  CCT     4790
Ala  Cys  Gln  Glu  Val  Lys  Val  Ser  Val  Ala  Ile  Glu  Asp  Leu  Glu  Pro
          1520                     1525                     1530

GAA  AAT  GGG  ATT  TTG  GAA  CTT  GAG  ACC  AAA  AGC  AGT  AAA  CTT  GTC  CAA     4838
Glu  Asn  Gly  Ile  Leu  Glu  Leu  Glu  Thr  Lys  Ser  Ser  Lys  Leu  Val  Gln
     1535                     1540                     1545

AAC  ATC  ATC  CAG  ACA  GCC  GTT  GAC  CAG  TTT  GTA  CGT  ACA  GAA  GAA  ACA     4886
Asn  Ile  Ile  Gln  Thr  Ala  Val  Asp  Gln  Phe  Val  Arg  Thr  Glu  Glu  Thr
1550                     1555                     1560                     1565

GCC  ACC  GAA  ATG  TTG  ACG  TCT  GAG  TTA  CAG  ACA  CAA  GCT  CAC  GTG  ATA     4934
Ala  Thr  Glu  Met  Leu  Thr  Ser  Glu  Leu  Gln  Thr  Gln  Ala  His  Val  Ile
                    1570                     1575                     1580

AAA  GCT  GAC  AGC  CAG  GAC  GCT  GGA  CAG  GAA  ACG  GAG  AAA  GAA  GGA  GAG     4982
Lys  Ala  Asp  Ser  Gln  Asp  Ala  Gly  Gln  Glu  Thr  Glu  Lys  Glu  Gly  Glu
               1585                     1590                     1595

GAA  CCT  CAG  GCC  TCT  GCA  CAG  GAT  GAA  ACA  CCA  ATT  ACT  TCA  GCC  AAA     5030
Glu  Pro  Gln  Ala  Ser  Ala  Gln  Asp  Glu  Thr  Pro  Ile  Thr  Ser  Ala  Lys
          1600                     1605                     1610

GAG  GAG  TCA  GAG  TCA  ACC  GCA  GTG  GGA  CAA  GCA  CAT  TCT  GAT  ATT  TCC     5078
Glu  Glu  Ser  Glu  Ser  Thr  Ala  Val  Gly  Gln  Ala  His  Ser  Asp  Ile  Ser
     1615                     1620                     1625

AAA  GAC  ATG  AGT  GAA  GCC  TCA  GAA  AAG  ACC  ATG  ACT  GTT  GAG  GTA  GAA     5126
Lys  Asp  Met  Ser  Glu  Ala  Ser  Glu  Lys  Thr  Met  Thr  Val  Glu  Val  Glu
1630                     1635                     1640                     1645

GGT  TCC  ACT  GTA  AAT  GAT  CAG  CAG  CTG  GAA  GAG  GTC  GTC  CTC  CCA  TCT     5174
Gly  Ser  Thr  Val  Asn  Asp  Gln  Gln  Leu  Glu  Glu  Val  Val  Leu  Pro  Ser
                    1650                     1655                     1660

GAG  GAA  GAG  GGA  GGT  GGA  GCT  GGA  ACA  AAG  TCT  GTG  CCA  GAA  GAT  GAT     5222
Glu  Glu  Glu  Gly  Gly  Gly  Ala  Gly  Thr  Lys  Ser  Val  Pro  Glu  Asp  Asp
               1665                     1670                     1675

GGT  CAT  GCC  TTG  TTA  GCA  GAA  AGA  ATA  GAG  AAG  TCA  CTA  GTT  GAA  CCG     5270
Gly  His  Ala  Leu  Leu  Ala  Glu  Arg  Ile  Glu  Lys  Ser  Leu  Val  Glu  Pro
```

-continued

```
                    1680                        1685                        1690
AAA  GAA  GAT  GAA  AAA  GGT  GAT  GAT  GTT  GAT  GAC  CCT  GAA  AAC  CAG  AAC        5318
Lys  Glu  Asp  Glu  Lys  Gly  Asp  Asp  Val  Asp  Asp  Pro  Glu  Asn  Gln  Asn
          1695                    1700                    1705

TCA  GCC  CTG  GCT  GAT  ACT  GAT  GCC  TCA  GGA  GGC  TTA  ACC  AAA  GAG  TCC        5366
Ser  Ala  Leu  Ala  Asp  Thr  Asp  Ala  Ser  Gly  Gly  Leu  Thr  Lys  Glu  Ser
1710                    1715                    1720                    1725

CCA  GAT  ACA  AAT  GGA  CCA  AAA  CAA  AAA  GAG  AAG  GAG  GAT  GCC  CAG  GAA        5414
Pro  Asp  Thr  Asn  Gly  Pro  Lys  Gln  Lys  Glu  Lys  Glu  Asp  Ala  Gln  Glu
                    1730                    1735                    1740

GTA  GAA  TTG  CAG  GAA  GGA  AAA  GTG  CAC  AGT  GAA  TCA  GAT  AAA  GCG  ATC        5462
Val  Glu  Leu  Gln  Glu  Gly  Lys  Val  His  Ser  Glu  Ser  Asp  Lys  Ala  Ile
          1745                    1750                    1755

ACA  CCC  CAA  GCA  CAG  GAG  GAG  TTA  CAG  AAA  CAA  GAG  AGA  GAA  TCT  GCA        5510
Thr  Pro  Gln  Ala  Gln  Glu  Glu  Leu  Gln  Lys  Gln  Glu  Arg  Glu  Ser  Ala
               1760                    1765                    1770

AAG  TCA  GAA  CTT  ACA  GAA  TCT   TAAAACATCA TGCAGTTAAA CTCATTGTCT                  5561
Lys  Ser  Glu  Leu  Thr  Glu  Ser
          1775                1780

GTTTGGAAGA  CCAGAATGTG  AAGACAAGTA  GTAGAAGAAA  ATGAATGCTG  CTGCTGAGAC               5621

TGAAGACCAG  TATTTCAGAA  CTTTGAGAAT  GGAGAGCAG   GCACATCAAC  TGATCTCATT               5681

TCTAGAGAGC  CCCTGACAAT  CCTGAGGCTT  CATCAGGAGC  TAGAGCCATT  TAACATTTCC               5741

TCTTTCCAAG  ACCAACCTAC  AATTTTCCCT  TGATAACCAT  ATAAATTCTG  ATTTAAGGTC               5801

CTAAATTCTT  AACCTGGAAC  TGGAGTTGGC  AATACCTAGT  TCTGCTTCTG  AAACTGGAGT               5861

ATCATTCTTT  ACATATTTAT  ATGTATGTTT  TAAGTAGTCC  TCCTGTATCT  ATTGTATATT               5921

TTTTTCTTAA  TGTTTAAGGA  AATGTGCAGG  ATACTACATG  CTTTTGTAT   CACACAGTAT               5981

ATGATGGGGC  ATGTGCCATA  GTGCAGGCTT  GGGGAGCTTT  AAGCCTCAGT  TATATAACCC               6041

ACAAAAAACA  GAGCCTCCTA  GATGTAACAT  TCCTGATCAA  GGTACAATTC  TTTAAAATTC               6101

ACTAATGATT  GAGGTCCATA  TTTAGTGGTA  CTCTGAAATT  GGTCACTTTC  CTATTACACG               6161

GAGTGTGCCA  AAACTAAAAA  GCATTTTGAA  ACATACAGAA  TGTTCTATTG  TCATTGGGAA               6221

ATTTTGCTTT  CTAACCCAGT  GGAGGTTAGA  AAGAAGTTAT  ATTCTGGTAG  CAAATTAACT               6281

TTACATCCTT  TTTCCTACTT  GTTATGGTTG  TTTGGACCGA  TAAGTGTGCT  TAATCCTGAG               6341

GCAAAGTAGT  GAATATGTTT  TATATGTTAT  GAAGAAAAGA  ATTGTTGTAA  GTTTTGATT                6401

CTACTCTTAT  ATGCTGGACT  GCATTCACAC  ATGGCATGAA  ATAAGTCAGG  TTCTTTACAA               6461

ATGGTATTTT  GATAGATACT  GGATTGTGTT  TGTGCCATAT  TTGTGCCATT  CCTTTAAGAA               6521

CAATGTTGCA  ACACATTCAT  TTGGATAAGT  TGTGATTTGA  CGACTGATTT  AAATAAAATA               6581

TTTGCTTCAC  TTAAAAAAAA  AAAA                                                         6605
```

( 2 ) INFORMATION FOR SEQ ID NO:5:

( i ) SEQUENCE CHARACTERISTICS:
        ( A ) LENGTH: 1780 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Gly  Ala  Gly  Ser  Ser  Thr  Glu  Gln  Arg  Ser  Pro  Glu  Gln  Pro  Pro
 1              5                        10                       15

Glu  Gly  Ser  Ser  Thr  Pro  Ala  Glu  Pro  Glu  Pro  Ser  Gly  Gly  Gly  Pro
            20                       25                       30
```

```
Ser Ala Glu Ala Ala Pro Asp Thr Thr Ala Asp Pro Ala Ile Ala Ala
         35                  40                  45
Ser Asp Pro Ala Thr Lys Leu Leu Gln Lys Asn Gly Gln Leu Ser Thr
     50                  55                  60
Ile Asn Gly Val Ala Glu Gln Asp Glu Leu Ser Leu Gln Glu Gly Asp
 65                  70                  75                   80
Leu Asn Gly Gln Lys Gly Ala Leu Asn Gly Gln Gly Ala Leu Asn Ser
                 85                  90                      95
Gln Glu Glu Glu Glu Val Ile Val Thr Glu Val Gly Gln Arg Asp Ser
                100                 105                110
Glu Asp Val Ser Glu Arg Asp Ser Asp Lys Glu Met Ala Thr Lys Ser
             115                 120                 125
Ala Val Val His Asp Ile Thr Asp Asp Gly Gln Glu Asn Arg Asn
         130                 135                 140
Ile Glu Gln Ile Pro Ser Ser Glu Ser Asn Leu Glu Glu Leu Thr Gln
145                 150                 155                 160
Pro Thr Glu Ser Gln Ala Asn Asp Ile Gly Phe Lys Lys Val Phe Lys
                 165                 170                 175
Phe Val Gly Phe Lys Phe Thr Val Lys Lys Asp Lys Thr Glu Lys Pro
             180                 185                 190
Asp Thr Val Gln Leu Leu Thr Val Lys Lys Asp Glu Gly Glu Gly Ala
         195                 200                 205
Ala Gly Ala Gly Asp His Gln Asp Pro Ser Leu Gly Ala Gly Glu Ala
    210                 215                 220
Ala Ser Lys Glu Ser Glu Pro Lys Gln Ser Thr Glu Lys Pro Glu Glu
225                 230                 235                 240
Thr Leu Lys Arg Glu Gln Ser His Ala Glu Ile Ser Pro Pro Ala Glu
                 245                 250                 255
Ser Gly Gln Ala Val Glu Glu Cys Lys Glu Glu Gly Glu Glu Lys Gln
             260                 265                 270
Glu Lys Glu Pro Ser Lys Ser Ala Glu Ser Pro Thr Ser Pro Val Thr
         275                 280                 285
Ser Glu Thr Gly Ser Thr Phe Lys Lys Phe Phe Thr Gln Gly Trp Ala
    290                 295                 300
Gly Trp Arg Lys Lys Thr Ser Phe Arg Lys Pro Lys Glu Asp Glu Val
305                 310                 315                 320
Glu Ala Ser Glu Lys Lys Lys Glu Gln Glu Pro Glu Lys Val Asp Thr
                 325                 330                 335
Glu Glu Asp Gly Lys Ala Glu Val Ala Ser Gly Lys Leu Thr Ala Ser
             340                 345                 350
Glu Gln Ala His Pro Gln Glu Pro Ala Glu Ser Ala His Glu Pro Arg
         355                 360                 365
Leu Ser Ala Glu Tyr Glu Lys Val Glu Leu Pro Ser Glu Glu Gln Val
    370                 375                 380
Ser Gly Ser Gln Gly Pro Ser Glu Glu Lys Pro Ala Pro Leu Ala Thr
385                 390                 395                 400
Glu Val Phe Asp Glu Lys Ile Glu Val His Gln Glu Glu Val Val Ala
                 405                 410                 415
Glu Val His Val Ser Thr Val Glu Glu Arg Thr Glu Glu Gln Lys Thr
             420                 425                 430
Glu Val Glu Glu Thr Ala Gly Ser Val Pro Ala Glu Glu Leu Val Gly
         435                 440                 445
Met Asp Ala Glu Pro Gln Glu Ala Glu Pro Ala Lys Glu Leu Val Lys
    450                 455                 460
```

```
Leu Lys Glu Thr Cys Val Ser Gly Glu Asp Pro Thr Gln Gly Ala Asp
465                 470                 475                 480

Leu Ser Pro Asp Glu Lys Val Leu Ser Lys Pro Pro Glu Gly Val Val
                485                 490                 495

Ser Glu Val Glu Met Leu Ser Ser Gln Glu Arg Met Lys Val Gln Gly
            500                 505                 510

Ser Pro Leu Lys Lys Leu Phe Thr Ser Thr Gly Leu Lys Lys Leu Ser
            515                 520                 525

Gly Lys Lys Gln Lys Gly Lys Arg Gly Gly Gly Asp Glu Glu Ser Gly
    530                 535                 540

Glu His Thr Gln Val Pro Ala Asp Ser Pro Asp Ser Gln Glu Glu Gln
545                 550                 555                 560

Lys Gly Glu Ser Ser Ala Ser Ser Pro Glu Glu Pro Glu Glu Ile Thr
                565                 570                 575

Cys Leu Glu Lys Gly Leu Ala Glu Val Gln Gln Asp Gly Glu Ala Glu
            580                 585                 590

Glu Gly Ala Thr Ser Asp Gly Glu Lys Lys Arg Glu Gly Val Thr Pro
    595                 600                 605

Trp Ala Ser Phe Lys Lys Met Val Thr Pro Lys Lys Arg Val Arg Arg
610                 615                 620

Pro Ser Glu Ser Asp Lys Glu Asp Glu Leu Asp Lys Val Lys Ser Ala
625                 630                 635                 640

Thr Leu Ser Ser Thr Glu Ser Thr Ala Ser Glu Met Gln Glu Glu Met
                645                 650                 655

Lys Gly Ser Val Glu Glu Pro Lys Pro Glu Glu Pro Lys Arg Lys Val
            660                 665                 670

Asp Thr Ser Val Ser Trp Glu Ala Leu Ile Cys Val Gly Ser Ser Lys
            675                 680                 685

Lys Arg Ala Arg Arg Ser Ser Asp Glu Glu Gly Gly Pro Lys
    690                 695                 700

Ala Met Gly Gly Asp His Gln Lys Ala Asp Glu Ala Gly Lys Asp Lys
705                 710                 715                 720

Glu Thr Gly Thr Asp Gly Ile Leu Ala Gly Ser Gln Glu His Asp Pro
            725                 730                 735

Gly Gln Gly Ser Ser Ser Pro Glu Gln Ala Gly Ser Pro Thr Glu Gly
            740                 745                 750

Glu Gly Val Ser Thr Trp Glu Ser Phe Lys Arg Leu Val Thr Pro Arg
            755                 760                 765

Lys Lys Ser Lys Ser Lys Leu Glu Glu Lys Ser Glu Asp Ser Ile Ala
    770                 775                 780

Gly Ser Gly Val Glu His Ser Thr Pro Asp Thr Glu Pro Gly Lys Glu
785                 790                 795                 800

Glu Ser Trp Val Ser Ile Lys Lys Phe Ile Pro Gly Arg Arg Lys Lys
                805                 810                 815

Arg Pro Asp Gly Lys Gln Glu Gln Ala Pro Val Glu Asp Ala Gly Pro
            820                 825                 830

Thr Gly Ala Asn Glu Asp Asp Ser Asp Val Pro Ala Val Val Pro Leu
            835                 840                 845

Ser Glu Tyr Asp Ala Val Glu Arg Glu Lys Met Glu Ala Gln Gln Ala
    850                 855                 860

Gln Lys Gly Ala Glu Gln Pro Glu Gln Lys Ala Ala Thr Glu Val Ser
865                 870                 875                 880

Lys Glu Leu Ser Glu Ser Gln Val His Met Met Ala Ala Ala Val Ala
```

-continued

```
                            885                         890                          895
Asp  Gly  Thr  Arg  Ala  Ala  Thr  Ile  Ile  Glu  Glu  Arg  Ser  Pro  Ser  Trp
                    900                         905                     910
Ile  Ser  Ala  Ser  Val  Thr  Glu  Pro  Leu  Glu  Gln  Val  Glu  Ala  Glu  Ala
               915                         920                    925
Ala  Leu  Leu  Thr  Glu  Glu  Val  Leu  Glu  Arg  Glu  Val  Ile  Ala  Glu  Glu
          930                         935                    940
Glu  Pro  Pro  Thr  Val  Thr  Glu  Pro  Leu  Pro  Glu  Asn  Arg  Glu  Ala  Arg
945                         950                         955                      960
Gly  Asp  Thr  Val  Val  Ser  Glu  Ala  Glu  Leu  Thr  Pro  Glu  Ala  Val  Thr
                    965                         970                          975
Ala  Ala  Glu  Thr  Ala  Gly  Pro  Leu  Gly  Ser  Glu  Glu  Gly  Thr  Glu  Ala
               980                         985                         990
Ser  Ala  Ala  Glu  Glu  Thr  Thr  Glu  Met  Val  Ser  Ala  Val  Ser  Gln  Leu
          995                         1000                       1005
Thr  Asp  Ser  Pro  Asp  Thr  Thr  Glu  Glu  Ala  Thr  Pro  Val  Gln  Glu  Val
     1010                        1015                         1020
Glu  Gly  Gly  Val  Pro  Asp  Ile  Glu  Glu  Gln  Glu  Arg  Arg  Thr  Gln  Glu
1025                        1030                        1035                        1040
Val  Leu  Gln  Ala  Val  Ala  Glu  Lys  Val  Lys  Glu  Glu  Ser  Gln  Leu  Pro
                    1045                        1050                        1055
Gly  Thr  Gly  Gly  Pro  Glu  Asp  Val  Leu  Gln  Pro  Val  Gln  Arg  Ala  Glu
               1060                        1065                        1070
Ala  Glu  Arg  Pro  Glu  Glu  Gln  Ala  Glu  Ala  Ser  Gly  Leu  Lys  Lys  Glu
          1075                        1080                        1085
Thr  Asp  Val  Val  Leu  Lys  Val  Asp  Ala  Gln  Glu  Ala  Lys  Thr  Glu  Pro
     1090                        1095                        1100
Phe  Thr  Gln  Gly  Lys  Val  Val  Gly  Gln  Thr  Thr  Pro  Glu  Ser  Phe  Glu
1105                        1110                        1115                        1120
Lys  Ala  Pro  Gln  Val  Thr  Glu  Ser  Ile  Glu  Ser  Ser  Glu  Leu  Val  Thr
                    1125                        1130                        1135
Thr  Cys  Gln  Ala  Glu  Thr  Leu  Ala  Gly  Val  Lys  Ser  Gln  Glu  Met  Val
               1140                        1145                        1150
Met  Glu  Gln  Ala  Ile  Pro  Pro  Asp  Ser  Val  Glu  Thr  Pro  Thr  Asp  Ser
          1155                        1160                        1165
Glu  Thr  Asp  Gly  Ser  Thr  Pro  Val  Ala  Asp  Phe  Asp  Ala  Pro  Gly  Thr
     1170                        1175                        1180
Thr  Gln  Lys  Asp  Glu  Ile  Val  Glu  Ile  His  Glu  Glu  Asn  Glu  Val  His
1185                        1190                        1195                        1200
Leu  Val  Pro  Val  Arg  Gly  Thr  Glu  Ala  Glu  Ala  Val  Pro  Ala  Gln  Lys
                    1205                        1210                        1215
Glu  Arg  Pro  Pro  Ala  Pro  Ser  Ser  Phe  Val  Phe  Gln  Glu  Glu  Thr  Lys
               1220                        1225                        1230
Glu  Gln  Ser  Lys  Met  Glu  Asp  Thr  Leu  Glu  His  Thr  Asp  Lys  Glu  Val
          1235                        1240                        1245
Ser  Val  Glu  Thr  Val  Ser  Ile  Leu  Ser  Lys  Thr  Glu  Gly  Thr  Gln  Glu
     1250                        1255                        1260
Ala  Asp  Gln  Tyr  Ala  Asp  Glu  Lys  Thr  Lys  Asp  Val  Pro  Phe  Phe  Glu
1265                        1270                        1275                        1280
Gly  Leu  Glu  Gly  Ser  Ile  Asp  Thr  Gly  Ile  Thr  Val  Ser  Arg  Glu  Lys
                    1285                        1290                        1295
Val  Thr  Glu  Val  Ala  Leu  Lys  Gly  Glu  Gly  Thr  Glu  Glu  Ala  Glu  Cys
               1300                        1305                        1310
```

Lys Lys Asp Asp Ala Leu Glu Leu Gln Ser His Ala Lys Ser Pro Pro
         1315                1320                1325

Ser Pro Val Glu Arg Glu Met Val Val Gln Val Glu Arg Glu Lys Thr
         1330                1335                1340

Glu Ala Glu Pro Thr His Val Asn Glu Glu Lys Leu Glu His Glu Thr
1345                1350                1355                1360

Ala Val Thr Val Ser Glu Glu Val Ser Lys Gln Leu Leu Gln Thr Val
                    1365                1370                1375

Asn Val Pro Ile Ile Asp Gly Ala Lys Glu Val Ser Ser Leu Glu Gly
              1380                1385                1390

Ser Pro Pro Pro Cys Leu Gly Gln Glu Ala Val Cys Thr Lys Ile
         1395                1400                1405

Gln Val Gln Ser Ser Glu Ala Ser Phe Thr Leu Thr Ala Ala Ala Glu
         1410                1415                1420

Glu Glu Lys Val Leu Gly Glu Thr Ala Asn Ile Leu Glu Thr Gly Glu
1425                1430                1435                1440

Thr Leu Glu Pro Ala Gly Ala His Leu Val Leu Glu Glu Lys Ser Ser
                    1445                1450                1455

Glu Lys Asn Glu Asp Phe Ala Ala His Pro Gly Glu Asp Ala Val Pro
                    1460                1465                1470

Thr Gly Pro Asp Cys Gln Ala Lys Ser Thr Pro Val Ile Val Ser Ala
         1475                1480                1485

Thr Thr Lys Lys Gly Leu Ser Ser Asp Leu Glu Gly Glu Lys Thr Thr
1490                1495                1500

Ser Leu Lys Trp Lys Ser Asp Glu Val Asp Glu Gln Val Ala Cys Gln
1505                1510                1515                1520

Glu Val Lys Val Ser Val Ala Ile Glu Asp Leu Glu Pro Glu Asn Gly
                    1525                1530                1535

Ile Leu Glu Leu Glu Thr Lys Ser Ser Lys Leu Val Gln Asn Ile Ile
                    1540                1545                1550

Gln Thr Ala Val Asp Gln Phe Val Arg Thr Glu Glu Thr Ala Thr Glu
         1555                1560                1565

Met Leu Thr Ser Glu Leu Gln Thr Gln Ala His Val Ile Lys Ala Asp
         1570                1575                1580

Ser Gln Asp Ala Gly Gln Glu Thr Glu Lys Glu Gly Glu Glu Pro Gln
1585                1590                1595                1600

Ala Ser Ala Gln Asp Glu Thr Pro Ile Thr Ser Ala Lys Glu Glu Ser
                    1605                1610                1615

Glu Ser Thr Ala Val Gly Gln Ala His Ser Asp Ile Ser Lys Asp Met
                    1620                1625                1630

Ser Glu Ala Ser Glu Lys Thr Met Thr Val Glu Val Glu Gly Ser Thr
         1635                1640                1645

Val Asn Asp Gln Gln Leu Glu Glu Val Val Leu Pro Ser Glu Glu Glu
         1650                1655                1660

Gly Gly Gly Ala Gly Thr Lys Ser Val Pro Glu Asp Asp Gly His Ala
1665                1670                1675                1680

Leu Leu Ala Glu Arg Ile Glu Lys Ser Leu Val Glu Pro Lys Glu Asp
                    1685                1690                1695

Glu Lys Gly Asp Asp Val Asp Asp Pro Glu Asn Gln Asn Ser Ala Leu
                    1700                1705                1710

Ala Asp Thr Asp Ala Ser Gly Gly Leu Thr Lys Glu Ser Pro Asp Thr
         1715                1720                1725

Asn Gly Pro Lys Gln Lys Glu Lys Glu Asp Ala Gln Glu Val Glu Leu
         1730                1735                1740

```
Gln Glu Gly Lys Val His Ser Glu Ser Asp Lys Ala Ile Thr Pro Gln
1745                1750                1755                1760

Ala Gln Glu Glu Leu Gln Lys Gln Glu Arg Glu Ser Ala Lys Ser Glu
              1765                1770                1775

Leu Thr Glu Ser
        1780
```

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Leu Glu Thr Lys Ser Ser Lys Leu Val Gln Asn Ile Ile Gln
1               5                   10
```

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Leu Ile Glu Thr Ala Ser Ser Leu Val Lys Asn Ala Ile Gln
1               5                   10
```

( 2 ) INFORMATION FOR SEQ ID NO:8:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Asp Leu Ile Glu Glu Ala Ala Ser Arg Ile Val Asp Ala Val Ile
1               5                   10                  15

Glu Gln Val Lys Ala Ala Gly Ala
                20
```

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CCGCCATGGT GCATATGTCC GAGTCCAGTG AGC                        33

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GCGCGGATCC GCACTCACTT TGACCTCCTG                           30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GCGCGGATCC GCTATCACGT GAGCTTGTGT 30

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CCGCCATGGT GCATATGGTA GCAATTGAGG ATTTAG 36

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GGAGGATCCA GAGATTCTGT AGTTCTG 27

( 2 ) INFORMATION FOR SEQ ID NO:14:

( i ) SEQUENCE CHARACTERISTICS:
        ( A ) LENGTH: 453 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
Glu Ser Ser Glu Leu Val Thr Thr Cys Gln Ala Glu Thr Leu Ala Gly
 1               5                  10                  15

Val Lys Ser Gln Glu Met Val Met Glu Gln Ala Ile Pro Pro Asp Ser
            20                  25                  30

Val Glu Thr Pro Thr Asp Ser Glu Thr Asp Gly Ser Thr Pro Val Ala
        35                  40                  45

Asp Phe Asp Ala Pro Gly Thr Thr Gln Lys Asp Glu Ile Val Glu Ile
    50                  55                  60

His Glu Glu Asn Glu Val His Leu Val Pro Val Arg Gly Thr Glu Ala
65                  70                  75                  80

Glu Ala Val Pro Ala Gln Lys Glu Arg Pro Pro Ala Pro Ser Ser Phe
                85                  90                  95

Val Phe Gln Glu Glu Thr Lys Glu Gln Ser Lys Met Glu Asp Thr Leu
                100                 105                 110

Glu His Thr Asp Lys Glu Val Ser Val Glu Thr Val Ser Ile Leu Ser
            115                 120                 125

Lys Thr Glu Gly Thr Gln Glu Ala Asp Gln Tyr Ala Asp Glu Lys Thr
        130                 135                 140

Lys Asp Val Pro Phe Phe Glu Gly Leu Glu Gly Ser Ile Asp Thr Gly
145                 150                 155                 160
```

```
Ile  Thr  Val  Ser  Arg  Glu  Lys  Val  Thr  Glu  Val  Ala  Leu  Lys  Gly  Glu
               165                      170                     175

Gly  Thr  Glu  Glu  Ala  Glu  Cys  Lys  Lys  Asp  Asp  Ala  Leu  Glu  Leu  Gln
                    180                 185                     190

Ser  His  Ala  Lys  Ser  Pro  Pro  Ser  Pro  Val  Glu  Arg  Glu  Met  Val  Val
          195                      200                     205

Gln  Val  Glu  Arg  Glu  Lys  Thr  Glu  Ala  Glu  Pro  Thr  His  Val  Asn  Glu
     210                      215                     220

Glu  Lys  Leu  Glu  His  Glu  Thr  Ala  Val  Thr  Val  Ser  Glu  Glu  Val  Ser
225                      230                     235                         240

Lys  Gln  Leu  Leu  Gln  Thr  Val  Asn  Val  Pro  Ile  Ile  Asp  Gly  Ala  Lys
               245                      250                     255

Glu  Val  Ser  Ser  Leu  Glu  Gly  Ser  Pro  Pro  Cys  Leu  Gly  Gln  Glu
               260                      265                     270

Glu  Ala  Val  Cys  Thr  Lys  Ile  Gln  Val  Gln  Ser  Ser  Glu  Ala  Ser  Phe
               275                      280                     285

Thr  Leu  Thr  Ala  Ala  Ala  Glu  Glu  Lys  Val  Leu  Gly  Glu  Thr  Ala
     290                      295                     300

Asn  Ile  Leu  Glu  Thr  Gly  Glu  Thr  Leu  Glu  Pro  Ala  Gly  Ala  His  Leu
305                      310                     315                         320

Val  Leu  Glu  Glu  Lys  Ser  Ser  Glu  Lys  Asn  Glu  Asp  Phe  Ala  Ala  His
               325                      330                     335

Pro  Gly  Glu  Asp  Ala  Val  Pro  Thr  Gly  Pro  Asp  Cys  Gln  Ala  Lys  Ser
               340                      345                     350

Thr  Pro  Val  Ile  Val  Ser  Ala  Thr  Thr  Lys  Lys  Gly  Leu  Ser  Ser  Asp
               355                      360                     365

Leu  Glu  Gly  Glu  Lys  Thr  Thr  Ser  Leu  Lys  Trp  Lys  Ser  Asp  Glu  Val
     370                      375                     380

Asp  Glu  Gln  Val  Ala  Cys  Gln  Glu  Val  Lys  Val  Ser  Val  Ala  Ile  Glu
385                      390                     395                         400

Asp  Leu  Glu  Pro  Glu  Asn  Gly  Ile  Leu  Glu  Leu  Glu  Thr  Lys  Ser  Ser
                    405                 410                     415

Lys  Leu  Val  Gln  Asn  Ile  Ile  Gln  Thr  Ala  Val  Asp  Gln  Phe  Val  Arg
               420                      425                     430

Thr  Glu  Glu  Thr  Ala  Thr  Glu  Met  Leu  Thr  Ser  Glu  Leu  Gln  Thr  Gln
          435                      440                     445

Ala  His  Val  Ile  Lys
450
```

(2) INFORMATION FOR SEQ ID NO:15:

(i) SEQUENCE CHARACTERISTICS:
        (A) LENGTH: 396 amino acids
        (B) TYPE: amino acid
        (C) STRANDEDNESS: single
        (D) TOPOLOGY: linear (xi) SEQUENCE DESCRIPTION: SEQ ID NO:15:

```
Glu  Ser  Ser  Glu  Leu  Val  Thr  Thr  Cys  Gln  Ala  Glu  Thr  Leu  Ala  Gly
1              5                        10                      15

Val  Lys  Ser  Gln  Glu  Met  Val  Met  Glu  Gln  Ala  Ile  Pro  Pro  Asp  Ser
               20                       25                      30

Val  Glu  Thr  Pro  Thr  Asp  Ser  Glu  Thr  Asp  Gly  Ser  Thr  Pro  Val  Ala
               35                       40                      45

Asp  Phe  Asp  Ala  Pro  Gly  Thr  Thr  Gln  Lys  Asp  Glu  Ile  Val  Glu  Ile
          50                       55                      60
```

His Glu Glu Asn Glu Val His Leu Val Pro Val Arg Gly Thr Glu Ala
65                  70                  75                  80

Glu Ala Val Pro Ala Gln Lys Glu Arg Pro Pro Ala Pro Ser Ser Phe
                85                  90                  95

Val Phe Gln Glu Glu Thr Lys Glu Gln Ser Lys Met Glu Asp Thr Leu
            100                 105                 110

Glu His Thr Asp Lys Glu Val Ser Val Glu Thr Val Ser Ile Leu Ser
        115                 120                 125

Lys Thr Glu Gly Thr Gln Glu Ala Asp Gln Tyr Ala Asp Glu Lys Thr
    130                 135                 140

Lys Asp Val Pro Phe Phe Glu Gly Leu Glu Gly Ser Ile Asp Thr Gly
145                 150                 155                 160

Ile Thr Val Ser Arg Glu Lys Val Thr Glu Val Ala Leu Lys Gly Glu
                165                 170                 175

Gly Thr Glu Glu Ala Glu Cys Lys Lys Asp Asp Ala Leu Glu Leu Gln
            180                 185                 190

Ser His Ala Lys Ser Pro Pro Ser Pro Val Glu Arg Glu Met Val Val
        195                 200                 205

Gln Val Glu Arg Glu Lys Thr Glu Ala Glu Pro Thr His Val Asn Glu
    210                 215                 220

Glu Lys Leu Glu His Glu Thr Ala Val Thr Val Ser Glu Glu Val Ser
225                 230                 235                 240

Lys Gln Leu Leu Gln Thr Val Asn Val Pro Ile Ile Asp Gly Ala Lys
                245                 250                 255

Glu Val Ser Ser Leu Glu Gly Ser Pro Pro Cys Leu Gly Gln Glu
            260                 265                 270

Glu Ala Val Cys Thr Lys Ile Gln Val Gln Ser Ser Glu Ala Ser Phe
        275                 280                 285

Thr Leu Thr Ala Ala Ala Glu Glu Lys Val Leu Gly Glu Thr Ala
    290                 295                 300

Asn Ile Leu Glu Thr Gly Glu Thr Leu Glu Pro Ala Gly Ala His Leu
305                 310                 315                 320

Val Leu Glu Glu Lys Ser Ser Glu Lys Asn Glu Asp Phe Ala Ala His
                325                 330                 335

Pro Gly Glu Asp Ala Val Pro Thr Gly Pro Asp Cys Gln Ala Lys Ser
            340                 345                 350

Thr Pro Val Ile Val Ser Ala Thr Thr Lys Lys Gly Leu Ser Ser Asp
        355                 360                 365

Leu Glu Gly Glu Lys Thr Thr Ser Leu Lys Trp Lys Ser Asp Glu Val
    370                 375                 380

Asp Glu Gln Val Ala Cys Gln Glu Val Lys Val Ser
385                 390                 395

( 2 ) INFORMATION FOR SEQ ID NO:16:

( i ) SEQUENCE CHARACTERISTICS:
( A ) LENGTH: 255 amino acids
( B ) TYPE: amino acid
( C ) STRANDEDNESS: single
( D ) TOPOLOGY: linear ( x i ) SEQUENCE DESCRIPTION: SEQ ID NO:16:

Val Ala Ile Glu Asp Leu Glu Pro Glu Asn Gly Ile Leu Glu Leu Glu
1               5                   10                  15

Thr Lys Ser Ser Lys Leu Val Gln Asn Ile Ile Gln Thr Ala Val Asp
            20                  25                  30

```
Gln  Phe  Val  Arg  Thr  Glu  Glu  Thr  Ala  Thr  Glu  Met  Leu  Thr  Ser  Glu
          35                  40                       45

Leu  Gln  Thr  Gln  Ala  His  Val  Ile  Lys  Ala  Asp  Ser  Gln  Asp  Ala  Gly
     50                  55                       60

Gln  Glu  Thr  Glu  Lys  Glu  Gly  Glu  Glu  Pro  Gln  Ala  Ser  Ala  Gln  Asp
65                  70                       75                            80

Glu  Thr  Pro  Ile  Thr  Ser  Ala  Lys  Glu  Glu  Ser  Glu  Ser  Thr  Ala  Val
               85                       90                            95

Gly  Gln  Ala  His  Ser  Asp  Ile  Ser  Lys  Asp  Met  Ser  Glu  Ala  Ser  Glu
               100                 105                      110

Lys  Thr  Met  Thr  Val  Glu  Val  Glu  Gly  Ser  Thr  Val  Asn  Asp  Gln  Gln
          115                 120                      125

Leu  Glu  Glu  Val  Val  Leu  Pro  Ser  Glu  Glu  Glu  Gly  Gly  Gly  Ala  Gly
     130                 135                           140

Thr  Lys  Ser  Val  Pro  Glu  Asp  Asp  Gly  His  Ala  Leu  Leu  Ala  Glu  Arg
145                      150                      155                      160

Ile  Glu  Lys  Ser  Leu  Val  Glu  Pro  Lys  Glu  Asp  Glu  Lys  Gly  Asp  Asp
               165                      170                      175

Val  Asp  Asp  Pro  Glu  Asn  Gln  Asn  Ser  Ala  Leu  Ala  Asp  Thr  Asp  Ala
               180                 185                      190

Ser  Gly  Gly  Leu  Thr  Lys  Glu  Ser  Pro  Asp  Thr  Asn  Gly  Pro  Lys  Gln
          195                      200                 205

Lys  Glu  Lys  Glu  Asp  Ala  Gln  Glu  Val  Glu  Leu  Gln  Glu  Gly  Lys  Val
     210                      215                      220

His  Ser  Glu  Ser  Asp  Lys  Ala  Ile  Thr  Pro  Gln  Ala  Gln  Glu  Glu  Leu
225                      230                 235                           240

Gln  Lys  Gln  Glu  Arg  Glu  Ser  Ala  Lys  Ser  Glu  Leu  Thr  Glu  Ser
               245                      250                      255
```

(2) INFORMATION FOR SEQ ID NO:17:

(i) SEQUENCE CHARACTERISTICS:
        (A) LENGTH: 651 amino acids
        (B) TYPE: amino acid
        (C) STRANDEDNESS: single
        (D) TOPOLOGY: linear (xi) SEQUENCE DESCRIPTION: SEQ ID NO:17:

```
Glu  Ser  Ser  Glu  Leu  Val  Thr  Thr  Cys  Gln  Ala  Glu  Thr  Leu  Ala  Gly
1                  5                       10                      15

Val  Lys  Ser  Gln  Glu  Met  Val  Met  Glu  Gln  Ala  Ile  Pro  Pro  Asp  Ser
          20                       25                      30

Val  Glu  Thr  Pro  Thr  Asp  Ser  Glu  Thr  Asp  Gly  Ser  Thr  Pro  Val  Ala
          35                  40                       45

Asp  Phe  Asp  Ala  Pro  Gly  Thr  Thr  Gln  Lys  Asp  Glu  Ile  Val  Glu  Ile
     50                  55                       60

His  Glu  Glu  Asn  Glu  Val  His  Leu  Val  Pro  Val  Arg  Gly  Thr  Glu  Ala
65                  70                       75                            80

Glu  Ala  Val  Pro  Ala  Gln  Lys  Glu  Arg  Pro  Pro  Ala  Pro  Ser  Ser  Phe
               85                       90                            95

Val  Phe  Gln  Glu  Glu  Thr  Lys  Glu  Gln  Ser  Lys  Met  Glu  Asp  Thr  Leu
               100                      105                      110

Glu  His  Thr  Asp  Lys  Glu  Val  Ser  Val  Glu  Thr  Val  Ser  Ile  Leu  Ser
          115                      120                      125

Lys  Thr  Glu  Gly  Thr  Gln  Glu  Ala  Asp  Gln  Tyr  Ala  Asp  Glu  Lys  Thr
     130                      135                      140
```

-continued

| | | | | | | | | | | | | | | |
|---|---|---|---|---|---|---|---|---|---|---|---|---|---|---|
| Lys 145 | Asp | Val | Pro | Phe 150 | Phe | Glu | Leu | Glu | Gly 155 | Ser | Ile | Asp | Thr | Gly 160 |
| Ile | Thr | Val | Ser | Arg 165 | Glu | Lys | Val | Thr 170 | Glu | Val | Ala | Leu | Lys 175 | Glu |
| Gly | Thr | Glu | Glu 180 | Ala | Glu | Cys | Lys | Lys 185 | Asp | Asp | Ala | Leu | Glu 190 | Leu | Gln |
| Ser | His | Ala 195 | Lys | Ser | Pro | Pro | Ser 200 | Pro | Val | Glu | Arg | Glu 205 | Met | Val | Val |
| Gln | Val 210 | Glu | Arg | Glu | Lys | Thr 215 | Glu | Ala | Glu | Pro | Thr 220 | His | Val | Asn | Glu |
| Glu 225 | Lys | Leu | Glu | His | Glu 230 | Thr | Ala | Val | Thr | Val 235 | Ser | Glu | Glu | Val | Ser 240 |
| Lys | Gln | Leu | Leu | Gln 245 | Thr | Val | Asn | Val | Pro 250 | Ile | Ile | Asp | Gly | Ala 255 | Lys |
| Glu | Val | Ser | Ser 260 | Leu | Glu | Gly | Ser | Pro 265 | Pro | Cys | Leu | Gly 270 | Gln | Glu |
| Glu | Ala | Val 275 | Cys | Thr | Lys | Ile | Gln 280 | Val | Gln | Ser | Ser | Glu 285 | Ala | Ser | Phe |
| Thr | Leu 290 | Thr | Ala | Ala | Ala | Glu 295 | Glu | Glu | Lys | Val | Leu 300 | Gly | Glu | Thr | Ala |
| Asn 305 | Ile | Leu | Glu | Thr | Gly 310 | Glu | Thr | Leu | Glu | Pro 315 | Ala | Gly | Ala | His | Leu 320 |
| Val | Leu | Glu | Glu | Lys 325 | Ser | Ser | Glu | Lys | Asn 330 | Glu | Asp | Phe | Ala | Ala 335 | His |
| Pro | Gly | Glu | Asp 340 | Ala | Val | Pro | Thr | Gly 345 | Pro | Asp | Cys | Gln | Ala 350 | Lys | Ser |
| Thr | Pro | Val 355 | Ile | Val | Ser | Ala | Thr 360 | Thr | Lys | Lys | Gly | Leu 365 | Ser | Ser | Asp |
| Leu | Glu 370 | Gly | Glu | Lys | Thr | Thr 375 | Ser | Leu | Lys | Trp | Lys 380 | Ser | Asp | Glu | Val |
| Asp 385 | Glu | Gln | Val | Ala | Cys 390 | Gln | Glu | Val | Lys | Val 395 | Ser | Val | Ala | Ile | Glu 400 |
| Asp | Leu | Glu | Pro | Glu 405 | Asn | Gly | Ile | Leu | Glu 410 | Leu | Glu | Thr | Lys | Ser 415 | Ser |
| Lys | Leu | Val | Gln 420 | Asn | Ile | Ile | Gln | Thr 425 | Ala | Val | Asp | Gln | Phe 430 | Val | Arg |
| Thr | Glu | Glu 435 | Thr | Ala | Thr | Glu | Met 440 | Leu | Thr | Ser | Glu | Leu 445 | Gln | Thr | Gln |
| Ala | His 450 | Val | Ile | Lys | Ala | Asp 455 | Ser | Gln | Asp | Ala | Gly 460 | Gln | Glu | Thr | Glu |
| Lys 465 | Glu | Gly | Glu | Glu | Pro 470 | Gln | Ala | Ser | Ala | Gln 475 | Asp | Glu | Thr | Pro | Ile 480 |
| Thr | Ser | Ala | Lys | Glu 485 | Glu | Ser | Glu | Ser | Thr 490 | Ala | Val | Gly | Gln | Ala 495 | His |
| Ser | Asp | Ile | Ser 500 | Lys | Asp | Met | Ser | Glu 505 | Ala | Ser | Glu | Lys | Thr 510 | Met | Thr |
| Val | Glu | Val 515 | Glu | Gly | Ser | Thr | Val 520 | Asn | Asp | Gln | Gln | Leu 525 | Glu | Glu | Val |
| Val | Leu 530 | Pro | Ser | Glu | Glu | Glu 535 | Gly | Gly | Ala | Gly | Thr 540 | Lys | Ser | Val |
| Pro 545 | Glu | Asp | Asp | Gly 550 | His | Ala | Leu | Leu | Ala 555 | Glu | Arg | Ile | Glu | Lys 560 | Ser |
| Leu | Val | Glu | Pro | Lys | Glu | Asp | Glu | Lys | Gly | Asp | Asp | Val | Asp | Asp | Pro |

|     |     |     |     | 565 |     |     |     |     | 570 |     |     |     |     | 575 |
| --- | --- | --- | --- | --- | --- | --- | --- | --- | --- | --- | --- | --- | --- | --- |

```
        Glu  Asn  Gln  Asn  Ser  Ala  Leu  Ala  Asp  Thr  Asp  Ala  Ser  Gly  Gly  Leu
                       580                      585                      590

Thr  Lys  Glu  Ser  Pro  Asp  Thr  Asn  Gly  Pro  Lys  Gln  Lys  Glu  Lys  Glu
                  595                      600                      605

Asp  Ala  Gln  Glu  Val  Glu  Leu  Gln  Glu  Gly  Lys  Val  His  Ser  Glu  Ser
                  610                      615                      620

Asp  Lys  Ala  Ile  Thr  Pro  Gln  Ala  Gln  Glu  Glu  Leu  Gln  Lys  Gln  Glu
        625                      630                      635                      640

Arg  Glu  Ser  Ala  Lys  Ser  Glu  Leu  Thr  Glu  Ser
                            645                      650
```

(2) INFORMATION FOR SEQ ID NO:18:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:18:

```
        Asp  Leu  Ile  Glu  Glu  Ala  Ala  Ser  Arg  Pro  Val  Asp  Ala  Val  Ile
        1              5                        10                       15

Glu  Gln  Val  Lys  Ala  Ala  Gly  Ala
                            20
```

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:19:

GACGAGATTG TGGAAATCCA TGAGG                        25

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:20:

GCGCGGATCC AGAGATTCTG TAGTTCTGAC                    30

(2) INFORMATION FOR SEQ ID NO:21:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:21:

```
        Phe  Lys  Lys  Phe  Phe  Thr  Gln  Gly  Trp  Ala  Gly  Trp  Arg  Lys  Lys  Thr
        1              5                        10                       15

Ser  Phe  Arg  Lys  Pro  Lys
                            20
```

(2) INFORMATION FOR SEQ ID NO:22:

(i) SEQUENCE CHARACTERISTICS:
  (A) LENGTH: 23 amino acids
  (B) TYPE: amino acid
  (C) STRANDEDNESS: single
  (D) TOPOLOGY: linear (xi) SEQUENCE DESCRIPTION: SEQ ID NO:22:

Pro Leu Lys Lys Leu Phe Thr Ser Thr Gly Leu Lys Lys Leu Ser Gly
1               5                   10                  15

Lys Lys Gln Lys Gly Lys Arg
            20

(2) INFORMATION FOR SEQ ID NO:23:

(i) SEQUENCE CHARACTERISTICS:
    (A) LENGTH: 22 amino acids
    (B) TYPE: amino acid
    (C) STRANDEDNESS: single
    (D) TOPOLOGY: linear (xi) SEQUENCE DESCRIPTION: SEQ ID NO:23:

Lys Ala Ser Met Leu Cys Phe Lys Arg Arg Lys Lys Ala Ala Lys Leu
1               5                   10                  15

Ala Lys Pro Lys Ala Gly
            20

(2) INFORMATION FOR SEQ ID NO:24:

(i) SEQUENCE CHARACTERISTICS:
    (A) LENGTH: 9 amino acids
    (B) TYPE: amino acid
    (C) STRANDEDNESS: single
    (D) TOPOLOGY: linear (xi) SEQUENCE DESCRIPTION: SEQ ID NO:24:

Val Arg Lys Arg Thr Leu Arg Arg Leu
1               5

PROTEIN BINDING FRAGMENTS OF GRAVIN

FIELD OF THE INVENTION

The present invention relates generally to proteins that maintain the subcellular localization of kinases. More specifically, this invention relates to polypeptide fragments of a protein, gravin, which binds to a regulatory subunit of cAMP-dependent protein kinase or to protein kinase C. The invention also relates to methods of modulating the interaction of gravin and its binding partners.

BACKGROUND OF THE INVENTION

Protein kinases are ubiquitous enzymes expressed in all eukaryotic cells and are involved in cellular responses to physiological stimuli. Protein kinases attach phosphate groups to substrate proteins. Cyclic-AMP (cAMP) dependent protein kinase (PKA) is an enzyme with broad substrate specificity which phosphorylates substrate proteins in response to cAMP. Protein kinase C (PKC) is an enzyme which phosphorylates substrate proteins in response to intracellular $Ca^{2+}$ and phospholipid.

Many hormones act through common signal transduction pathways that generate the intracellular second messenger cAMP. The predominant action of cAMP is to activate a PKA by binding to the regulatory subunit (R) dimer of the holoenzyme thereby releasing the catalytic (C) subunit. Free C subunit potentiates hormonal responses by phosphorylating substrate proteins near the site of kinase activation.

Two classes of the R subunit have been identified; RI and RII subunits which respectively form the type I and type II PKA holoenzymes. The subcellular distributions of PKA isoforms appear to be distinct. The RI isoforms (RIα and RIβ) are reported to be predominantly cytoplasmic and are excluded from the nuclear compartment, whereas up to 75% of the RII isoforms (RIIα or RIIβ) are particulate and associate with the plasma membrane, cytoskeletal components, secretory granules, the golgi apparatus, centrosomes and/or possibly nuclei.

Intracellular transduction of signals from the plasma membrane to specific subcellular compartments is a complex and highly regulated series of events which control essential physiological processes. An example of signaling pathway involvment essential in maintaining cellular homeostasis appears in Hunter, Cell, 80:225-236 (1995) where it was shown that many transforming oncogenes encode signal transduction components such as low molecular weight G proteins, protein kinases, or phosphatases. Phosphatases remove phosphate groups from proteins or other compounds. Kinase and phosphatase activities thus control intracellular signal transduction by phosphorylating and dephosphorylating substrate molecules. Now that many genes encoding these proteins have been identified, research emphasis has begun to focus on how these enzymes interface to control cellular events. A critical element in this operation is the subcellular location of each signaling enzyme. For example, Newton, Current Biology, 6:806–809 (1996) showed that the correct intracellular targeting of kinases and phosphatases directs these enzymes to their preferred substrates and reduces indiscriminate background phosphorylation and dephosphorylation.

Kinase and phosphatase targeting is achieved through association with targeting proteins or subunits [reviewed by Faux and Scott, TIBS, 21:312–315 (1996b)]. For example, tyrosine kinase (PTK) and tyrosine phosphatase (PTPase) activity are coupled to downstream cytoplasmic enzymes through adaptor proteins that contain SH2 and SH3 domains. SH2 domains recognize certain phosphotyrosyl residues and SH3 domains bind to a PXXP motif found in some kinases and phosphatases. Modular adaptor proteins like Grb2, p85, IRS-1, Crk and Nck comprise a single SH2 domain that recognizes phosphotyrosyl residues of signalling enzymes and two SH3 domains that bind to the PXXP motif on a separate set of target proteins. Similarly, many phospholipases, kinases, phosphatases and heterotrimeric G-proteins are targeted by specific membrane-targeting motifs such as the LIM, C2, pleckstrin homology and lipid anchoring domains [Gill, Structure, 3:1285–1289 (1995); Newton, Current Biology, 5:973–976 (1995)]. Through these interactions, signaling complexes assemble around receptor kinases or scaffold proteins to mediate cellular processes including hormone signaling events and immune cell function [Harrison et al., TIBS, 20:1213–1221 (1995)].

Until recently, second messenger-stimulated kinases and phosphatases were thought to be localized through association with individual targeting proteins. For example, three classes of phosphatase targeting subunits have been identified which are specific for protein phosphatase I [Chen et al. FEBS Letters, 356:51–55 (1994)]; protein phosphatase 2A [Csortos et al., J. Biol. Chem., 271:2578–2588 (1996)]; or protein phosphatase 2B [Shibasaki et al., Nature, 382:370–373 (1996)]. Likewise, three classes of PKC targeting proteins have been identified in Chapline et al., J. Biol. Chem. 268:6858–6861 (1993); Mochly-Rosen, Science, 268:247–251, 1995; and Staudinger et al., J. Cell Biol., 128:263–271 (1995). Compartmentalization of PKA is achieved through interaction of the R subunits with a functionally related family of thirty or so A-Kinase Anchoring Proteins, called AKAPs [reviewed in Scott and McCartney, Molecular Endocrinology, 8:5–13 (1994)]. The present invention contemplates that anchoring proteins confer specificity on serine/threonine kinases and phosphatases by directing these enzymes to discrete subcellular sites where they have restricted access to certain substrates and are optimally positioned to respond to fluctuations in the levels of second messengers.

A variation on this theme was reported in the recent identification of multivalent binding proteins that coordinate the location of serine/threonine kinase and phosphatase signaling complexes. For example, Herskowitz, Cell, 80:187–197 (1995) showed that the pheromone mating response in yeast is initiated through a G-protein linked receptor that activates a yeast MAP kinase cascade. This process proceeds efficiently because each enzyme in the cascade is associated with a scaffold protein called sterile 5 (STE 5) [Choi et al., Cell, 78:499–512, (1994)]. Clustering of successive members in the MAP kinase cascade allows for the tight regulation of the pathway and prevents "crosstalk" between the six functionally distinct MAP kinase modules in yeast [Herskowitz et al., 1995]. Another example of a multivalent binding protein is AKAP79 which targets PKA, PKC and protein phosphatase 2B at the postsynaptic densities of mammalian synapses [Klauck et al., Science, 271:1589–1592 (1996); Coghlan, et al., (1995b). The structure of AKAP79 is modular and resembles STE 5. Deletion analysis, peptide studies and co-precipitation studies of AKAP79 and STE5 have demonstrated that enzymes bind to distinct regions of the anchoring protein [Klauck et al., 1996]. Targeting of the AKAP79 signaling complex to the postsynaptic densities suggests a model for reversible phosphorylation in which the opposing effects of kinase and phosphatase action are co-localized by a common anchoring protein [Coghlan et al., Advances in Protein Phosphatases, 6:51–61 (1995a)].

AKAPs have been identified in a variety of organisms. At least seven proteins that bind the regulatory subunit of PKA in *Aplysia californica*, a marine invertebrate, have been identified [Cheley et at., *J. Biol. Chem.*, 269:2911–2920 (1994)]. One of these proteins is enriched in crude membrane fractions and taxol-stabilized microtubules and may thus anchor microtubules to the cell membrane as well as bind PKA. A mammalian AKAP microtubule-associated protein 2 (MAP2) attaches PKA to the cytoskeleton [DeCamilli et al., *J. Cell Biol.*, 103:189–203 (1986)]. The PKA-binding site on MAP2 is a 31-residue peptide in the amino-terminal region of the MAP2 molecule [Rubino et al., *Neuron*, 3:631–638 (1989)].

To date, a number of AKAPs have been identified which apparently bind PKA by a common secondary structure motif that includes an amphipathic helix region [Scott and McCartney, 1994]. Binding of PKA to most, if not all, identified AKAPs can be blocked in the presence of a peptide (Ht31) (SEQ ID NO: 8) that mimics the common secondary structure, while a mutant Ht31 peptide containing a single amino acid substitution (SEQ ID NO: 18) that disrupts the secondary structure of the peptide has no effect on PKA/AKAP binding [Carr et al., *J. Biol. Chem.*, 266:14188–14192 (1991)]. Even though PKA/AKAP interaction is effected by a common secondary structure, AKAPs (or homologous AKAPs found in different species) generally have unique primary structure as is evidenced by the growing number of AKAPs that have been identified in a variety of organisms. The unique structure in each anchoring protein confers specificity on a kinase by targeting an AKAP signalling complex to specific intracellular locations.

Chapline and co-workers recently reported the cloning of a PKC binding protein identified as "clone 72" [Chapline et al., *J. Biol. Chem.*, 271:6417–6422 (1996)]. Interestingly, Clone 72 was shown to have substantial homology to a mitogenic regulatory gene identified as "clone 322" [Lin et al., *Mol. Cell. Biol.*, 15:2754–2762 (1995)]. Clone 322 was identified as being the same molecule identified as "SSeCKS" in Lin, et al., *J. Biol. Chem.* 271:28340–28348 (1996). Clone 322 was shown to be down-regulated in oncogene (e.g., src, ras, fos and myc) transformed cells and thus appears to be a tumor suppressor gene.

Also of interest to the invention is Myasthenia gravis (MG), a disease of neuromuscular transmission characterized by weakness and rapid fatigability of the muscles. It is believed that MG is an autoimmune disease in which the patient develops antibodies to the nicotinic acetylcholine receptor. The nicotinic acetylcholine receptor controls a cation channel in response to binding of acetylcholine. In addition, development of autoantibodies to other cytoskeletal antigens including alpha actinin, actin, filamin and vinculin is observed in the MG patient. The muscle weakness appears to be caused by a failure of the nicotinic acetylcholine receptor as the autoantibodies apparently participate in destruction of the nicotinic acetylcholine receptors.

A previously unknown MG antigen, gravin, was identified by expression screening of a cDNA library with serum from a patient suffering from MG [Gordon et al., *J. Clin. Invest.*, 90:992–999 (1992)]. Gordon, et al. disclosed amino acid sequences disclosing 306 C-terminal amino acid residues of gravin and the corresponding polynucleotide. Gravin was shown to be expressed on the cell cortex and was also shown to be expressed in migratory cells such as fibroblasts and neurons, but not in stationary cells such as epithelial cells. In addition, gravin was found to be expressed in adherent cells, but not in non-adherent cells. Therefore, gravin was postulated to play a role in cell migration and/or cellular adhesion [Grove et al., *Anat. Rec.*, 239:231–242 (1994)].

There continues to exist a need in the art for further insights into the nature, function, and distribution of anchoring proteins and the role of anchoring proteins in myasthenia gravis.

SUMMARY OF THE INVENTION

This present invention is based on the discovery that gravin is a kinase anchoring protein that binds to the type II regulatory subunits of PKA and to PKC. The complete amino acid sequence of gravin is provided herein. In binding to protein kinases, gravin localizes kinases to a specific subcellular region(s) and may regulate the function of the kinases and thereby control cellular signalling.

In one aspect, the present invention provides a gravin polypeptide fragment that binds to the type II regulatory subunit of PKA. Preferably, the polypeptide fragment comprises amino acid residues 1526–1582 (SEQ ID NO: 1) of gravin. More preferably, the polypeptide fragment comprises amino acid residues 1537–1563 (SEQ ID NO: 2) of gravin.

In another aspect, the present invention provides a polypeptide fragment that binds to PKC. Preferably, the polypeptide fragment comprises amino acid residues 265–556 (SEQ ID NO: 3) of gravin.

Yet another aspect of this invention provides polypeptide analogs of such fragments. Analogs are fragments in which additions, substitutions, including conservative substitutions, or deletions of amino acid residues have been made in order to increase or decrease the binding affinity of the analog fragment for a protein kinase. These analogs of gravin may be useful for modulating (i.e., blocking, inhibiting, or stimulating) the interaction between gravin and the kinase.

The polypeptides of the present invention are synthesized in solution or on a solid support in accordance with conventional techniques as described in Stewart and Young, *Solid Phase Peptide Synthesis*, 2nd ed., Pierce Chemical Company, (1984) or Tam et al., *J. Am. Chem. Soc.*, 105:6442 (1983), both of which are incorporated herein by reference.

The polypeptides of this invention may be modified to facilitate passage into the cell, such as by conjugation to a lipid soluble moiety. For example, the peptides may be conjugated to myristic acid. The peptides may be myristoylated by standard techniques as described in Eichholtz et al., *J. Biol. Chem.* 268:1982–1986 (1993), incorporated herein by reference. Alternatively, the peptides may be packaged in liposomes that may fuse with cell membranes and deliver the peptides into the cells. Encapsulation of the peptides in liposomes may also be performed by standard techniques as generally described in U.S. Pat. Nos. 4,766,046; 5,169,637; 5,180,713; 5,185,154; 5,204,112; and 5,252,263 and PCT Patent Application No. 92/02244, each of which is incorporated herein by reference.

Another aspect of the invention provides polynucleotides encoding the protein binding fragments of gravin. Polynucleotides of the invention include DNA (i.e., genomic, complementary, and synthetic) and RNA. Sense and antisense polynucleotides, complementary to coding and noncoding polynucleotides are also contemplated. The polynucleotides of the present invention can be generated and purified by any number of standard, well-known techniques in the art. Also contemplated are polynucleotides which code for the polypeptides of the present invention based upon degeneracy of the genetic code. In addition, polynucleotides which encode gravin (e.g., degenerate oligomers) useful in polymerase chain reaction (PCR) technologies are contemplated. Polynucleotides encoding analogs of gravin or structurally related DNAs which hybridize under stringent hybridization conditions to the polynucleotides of the invention are also contemplated. Those of ordinary skill in the art will understand hybridization conditions described as "stringent."

Exemplary stringent hybridization conditions are as follows: hybridization at about 65° C. in 3X SSC, 20 mM NaPO₄ pH 6.8 and washing at about 65° C. in 0.2X SSC. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47–9.51 in *Molecular Cloning*, Cold Spring Harbor Laboratory Press, Cold Spring Harbor, N.Y. (1989).

Polynucleotides of the invention are useful for recombinant production of the kinase binding domain polypeptides. Vectors comprising polynucleotides encoding a kinase binding domain as well as promotor, selectable marker and other well-known vector components (e.g. origin of replication, multiple cloning sites, etc.) are also contemplated by the invention.

The skilled artisan will understand the various components of vectors, methods for manipulating and the uses of vectors in transforming or transfecting of host cells (prokaryotic and eukaryotic) and expressing the kinase binding domains of the present invention. Host cells, especially unicellular host cells such as procaryotic and eukaryotic cells, are stably or transiently transformed or transfected with DNAs of the invention in a manner allowing expression of the kinase binding fragments of gravin. Host cells of the invention are conspicuously useful in methods for the large scale production of protein binding fragments of gravin wherein the cells are grown in a suitable culture medium and the desired fragments are isolated from the cells or from the medium in which the cells are grown. Use of mammalian host cells is expected to provide for such post-translational modifications (e.g., myristoylation, glycosylation, proteolytic processing, lipidation and tyrosine, serine or threonine phosphorylation) as may be needed to confer biological activity on recombinant expression products of the invention.

Another aspect of this invention provides antibody substances (e.g., polyclonal and monoclonal antibodies, antibody fragments, single chain antibodies, chimeric antibodies, CDR-grafted antibodies, humanized antibodies and the like) specifically immunoreactive with the protein binding domains of gravin. Antibody substances can be prepared by standard techniques using isolated naturally-occurring or recombinant gravin. The antibody substances are useful in modulating (i.e., blocking, inhibiting, or stimulating) the binding between gravin and the kinase and in detecting gravin in patients suffering from MG. In addition, cell lines, (e.g., hybridomas), or cell lines transformed with recombinant expression constructs which produce antibody substances of the invention are contemplated.

In another aspect, methods of identifying a modulator compound that inhibits or increases binding between a gravin polypeptide and a gravin binding partner (e.g., type II regulatory subunit of PKA or PKC) are contemplated. In one method, gravin or a polypeptide fragment thereof such as set out in SEQ ID NOs: 1, 2 or 3 and a binding partner are incubated in the presence and absence of a putative modulator compound under conditions suitable for binding. The amount of binding in the presence and in the absence of the putative test compound is determined and compared. A reduction in the amount of binding observed in the presence of the test compound indicates that the test compound is an inhibitor. An increase in the amount of binding observed in the presence of the test compound indicates that the test compound increases binding between gravin and the binding partner. In one embodiment, either gravin or the binding partner can be immobilized on a solid substrate, and either gravin or the binding partner is delectably labeled. In addition, other assays, such as scintillation proximity assays may also be employed.

Modulators are useful for example, in inhibiting localization of a gravin binding partner (e.g. PKA, PKC, or other kinases) to a specific subcellular location. The contemplated modulators include polypeptides, polypeptide fragments of gravin and other organic and inorganic compounds.

The DNA sequence information provided by the present invention also makes possible the development, by homologous recombination or "knockout" strategies [see e.g. Capecchi, *Science* 244:1288–1292 (1989)] of mammals that fail to express functional gravin or that express an analog of gravin. The mammals of the present invention comprise a disruption of the gravin gene of the mammal or the disruption of a homolog of the gravin gene. The general strategy utilized to produce the mammals of the present invention involves the preparation of a targeting construct comprising DNA sequences homologous to the endogenous gene to be disrupted. The targeting construct is then introduced into embryonic stem cells (ES cells) whereby it integrates into and disrupts the endogenous gene or homolog thereof. After selecting cells which include the desired disruption, the selected ES cells are implanted into an embryo at the blastocyst stage. Exemplary mammals include rodent species.

Numerous additional aspects and advantages of the present invention will be apparent from the following detailed description of illustrative embodiments thereof.

DETAILED DESCRIPTION OF THE INVENTION

Figure 1A:
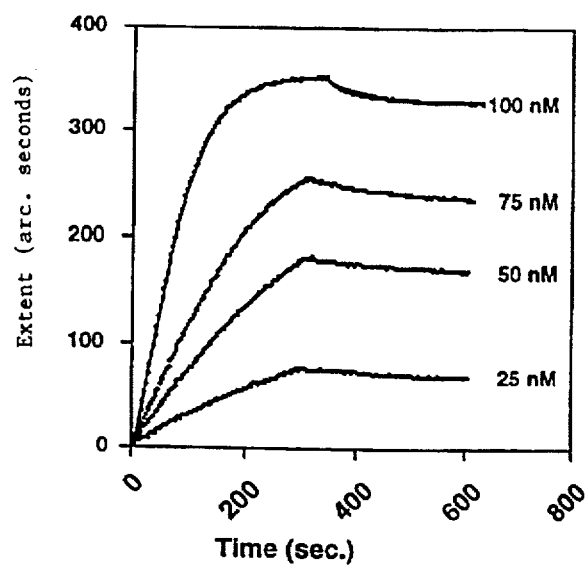
FIG. 1A shows the observed binding between gravin and RIIα as measured by surface plasmon resonance (SPR). The binding of R11α to an immobilized gravin fragment was measured in the presence of the indicated concentrations of RIIα.

The present invention is illustrated by the following examples. Example 1 describes the cloning and characterization of a cDNA encoding gravin. The mapping and identification of a fragment of gravin that binds to the type II regulatory subunit of PKA is disclosed in Example 2. Example 3 describes the mapping and identification of a PKC binding fragment of gravin. Example 4 discusses the preparation of monoclonal and polyclonal antibodies. Experiments describing gravin expression in human erythroleukemia cells (HEL) is provided in Example 5. Example 6 describes the role of gravin in signal transduction and Example 7 describes gravin's role in cell adhesion. In light of the present disclosure, those of skill in the art will appreciate that the following examples are intended to be illustrative only and that numerous changes, modifications and alterations can be made without departing from the spirit and scope of the invention.

EXAMPLE 1

To isolate cDNAs encoding potential RII binding proteins, a human fetal brain λ-ZAP cDNA library was screened by a modified overlay procedure using radiolabeled RIIα as a probe [Lohmann et al., *Proc. Natl. Acad. Sci. U.S.A.*, 81:6723–6727 (1984)]. Eight RII binding clones were identified, plaque purified and the ends of each insert were sequenced. Two of the clones represented known sequences. One matched MAP2, a previously identified AKAP [Theurkauf et al., *J. Biol. Chem.*, 257:3284–3290 (1982)]. The 3' end of another clone, designated HF 9, was identical to a previously described partial clone encoding gravin, which was originally isolated by screening a Human Umbilical Vein Endothelial cell (HUVE) cDNA library with serum from a Myasthenia gravis patient [Gordon et al., 1992].

Further sequencing of clone HF 9 showed that the cDNA insert was 3023 base pairs in length and encoded a continuous open reading frame of 651 amino acids. Northern blot analysis using a $^{32}$P random primed 1676 base pair Eco RI-Spe I fragment of HF 9 as a probe indicated that gravin mRNA was selectively expressed in certain human tissues. Two predominant mRNA species of 8.4 kb and 6.7 kb were detected in all tissues but predominated in liver, brain and lung, whereas an additional 5.5 kb message was detected in brain. The larger sizes of all the gravin messages, indicated that the HF 9 clone represented a partial cDNA. Therefore, the 1676 base pair HF 9 fragment was used to further screen the human fetal brain cDNA library for more complete transcripts. Five additional clones were obtained that yielded an additional 600 base pairs of coding region. As an alternative strategy, a human heart cDNA library was screened with the same 1676 base pair HF 9 fragment. Of the five positive clones isolated from the heart cDNA library, the longest clone contained a 4216 base pair insert, which overlapped with the 5' end of HF 9. This provided a contiguous composite sequence of 6605 base pairs encoding a protein of 1780 amino acids. The complete DNA and amino acid sequences of this protein, human gravin, are presented in SEQ ID NO: 4 and 5, respectively.

EXAMPLE 2

The last 651 amino acids of gravin were demonstrated to contain a binding site for association with the type II regulatory subunit of PKA. It was previously shown that regions of conserved secondary structure which are likely to include amphipathic α-helices are responsible for RII-binding [Carr et al., *J. Biol. Chem.*, 267:13376–13382 (1992)]. Residues 1540–1553 LETKSSKLVQNIIQ (SEQ ID NO: 6) of gravin fulfilled these criteria. These residues also show sequence identity with corresponding regions in other AKAPs and a helical-wheel plot suggested that there was a segregation of hydrophobic and hydrophilic sidechains which is compatible with the formation of an amphipathic helix. The RIIα binding fragment of gravin also shows some sequence homology to the corresponding RII binding regions in AKAP79 (LIETASSLVKNAIQ) (SEQ ID NO: 7) and in Ht31 (DLIEEAASRIVDAVIEQVKAAGA) (SEQ ID NO: 8). Ht31 is a sequence derived from human thyroid AKAP.

To identify the RII binding site(s) of gravin, a family of recombinant DNAs encoding fragments of gravin were generated by PCR using HF9 as the template. The polynucleotides encoding these fragments were subcloned into the pET16d plasmid which provides nucleotide sequences encoding a histine tag expressed at the amino terminus of the expressed gravin fragment. These constructs were expressed in *E. coli* and purified using the pET16d Histag bacterial expression/affinity purification system. Constructs encoding putative RII-binding site residues 1130–1582 (SEQ ID NO: 17) and 1130–1525 (SEQ ID NO: 15) of gravin were generated by utilizing a common 5' primer, CCGCCATGGTGCATATGTCCGAGTCCAGTGAGC, (SEQ ID NO: 9) but utilized distinct 3' primers: GCGCG-GATCCGCACTCACTTTGACCTCCTG (SEQ ID NO: 10) for residues 1130–1525 (SEQ ID NO: 15) and GCGCG-GATCCGCTATCACGTGAGCTTGTGT (SEQ ID NO: 11) for residues 1130–1582 (SEQ ID NO: 14). The 1526–1780 (SEQ ID NO: 16) construct was prepared by using the 5' primer, CCGCCATGGTGCATATGGTAGCAAT-TGAGGATTTAG (SEQ ID NO: 12) in conjunction with the 3' primer, GGAGGATCCAGAGATTCTGTAGTTCTG (SEQ ID NO: 13) used to subclone the full length clone. Each gravin construct was transfected into *E. coli* and the expression of recombinant Histag fusion proteins was induced by IPTG. Each recombinant protein was purified according to previously published methods [Coghlan et al., *Science*, 267:108–111 (1995b)].

The gravin fragments were screened for RIIα binding using an overlay procedure essentially as described in Lohman et al., *Proc. Nat. Acad. Sci.*, 81:6723–6727 (1984). Briefly, the overlay procedure is performed as follows. Protein samples are separated by SDS polyacrylamide gel electrophoresis (PAGE) and transferred to nitrocellulose by standard electrotransfer techniques. The immobilized protein is partially renatured by incubation in a blocking solution containing milk proteins then probed with $^{32}$P-labelled RII probe. After removal of unbound probe by washing, binding between gravin polypeptide fragments and RII is detected by autoradiography. To increase sensitivity of the assay (up to ten-fold), bound RII is detected immunologically (e.g. anti-RII-antisera and $^{125}$I-protein A, or monoclonal antibodies which specifically recognize RII.)

The 452 residue fragment encompassing residues 1130–1582 (SEQ ID NO: 14) bound $^{32}$P-radiolabeled RIIα in the overlay, whereas a smaller fragment, residues 1130–1525 (SEQ ID NO: 15), which lacked the RII-binding region was unable to bind RIIα.

Two additional experiments provided evidence that the putative amphipathic helix region was sufficient for RII-binding. The fragment encompassing residues 1526–1780 (SEQ ID NO: 16) of gravin bound RII in the overlay and a synthetic peptide covering residues 1537–1563 (SEQ ID NO: 2) blocked all RII-binding in the overlay. In addition, the anchoring protein inhibitor peptide Ht31 (DLIEEAASRIVDAVIEQVKAAGA) (SEQ ID NO: 8) which is a competitive inhibitor of RII/AKAP interactions also blocked RII binding to gravin as assessed by the overlay assay. Control experiments in which overlays were performed in the presence of 0.3 µM inhibitor polypeptide Ht31 (SEQ ID NO: 8) confirmed that the Ht31 inhibited binding between gravin and RIIα. In addition a second control peptide, Ht31 -pro, (DLIEEAASRPVDAVIEQVKAAGA) (SEQ ID NO: 18) which is unable to block RII/AKAP binding was unable to inhibit binding between gravin and RIIα. The second control peptide (SEQ ID NO: 18) is the Ht31 peptide in which an isoleucine has been replaced by a proline thereby disrupting the secondary structure. The Ht31 (SEQ ID NO: 8) peptide and Ht31-pro peptide were synthesized. To facilitate labeling and/or tracking of the control peptides, an additional tyrosine (radioiodination) or lysine (biotin/avidin) residue was sometimes included at the C-terminus of the control peptides. This data demonstrates that gravin is an AKAP and its principle RII-binding site is encompassed by residues 1526–1582 (SEQ ID NO: 1).

Figure 1B:
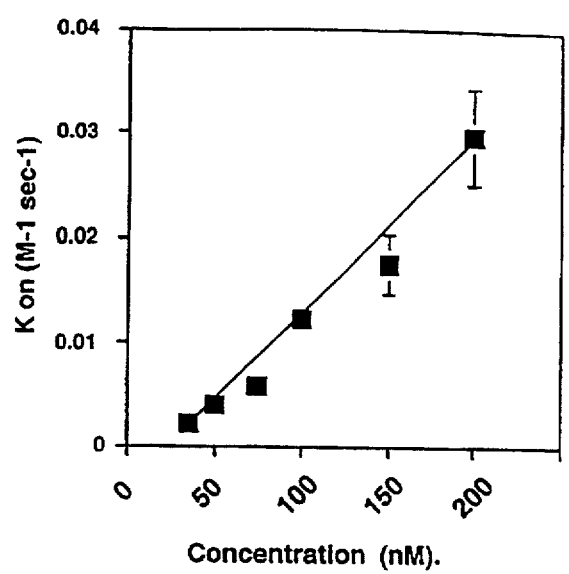
FIG. 1B shows the observed first order binding constants between gravin and RIIα at the indicated RIIα concentrations. (See Example 2).

This finding was further confirmed when the binding affinity of the gravin 1526–1780 (SEQ ID NO: 16) fragment for a recombinant fragment of RIIα was measured by surface plasmon resonance (SPR). SPR is an analytical technique that utilizes evanescent light to examine macromolecular complexes. The binding affinities of one protein to an immobilized binding partner can be measured by SPR. A recombinant fragment encompassing residues 1526–1780 (SEQ ID NO: 16) of gravin was coupled to a carboxymethyldextran IAsys cuvette using standard EDC/NHS coupling chemistry [Davies et al., *Techniques in Protein Chemistry*, 5:285–2992 (1994)]. The cuvette was activated by treating with 0.4M EDC/0.1M NHS for 8 min and washed extensively with PBST (PBS+0.05% Tween-20). Coupling of the gravin 1526–1780 fragment (SEQ ID NO: 16) (25 µg/ml) was accomplished in 10 mM formate buffer, pH 3.6 for 10 min at room temperature. Uncoupled protein was washed out with PBST and free amines were blocked with 1M ethanolamine, pH 8.5 for 2 min at room temperature. After washing with PBST, a stable baseline was established for 10 min before data collection. All binding experiments were performed with a recombinant fragment of RIIα (RII 1–45) [Scott, et al., *Pro. Nat. Acad. Sci.* 84:5192–5196 (1987)] which binds AKAPs with a similar affinity as the full-length protein. Previous experiments have indicated that release of RIIα 1–45 from the binding surface can be performed under conditions that are less harmful to the immobilized anchoring protein than studies using full length RII. Binding experiments were performed over a range of concentrations from 25 to 150 nM in volumes of 200 µl. The binding surface was regenerated between binding measurements using 60% ethanol with no decrease in extent measurements over the duration of an experiment. Data collection was done over three second intervals and was analyzed using the Fastfit™ software which was provided with the IAsys instrument. The binding properties of the immobilized gravin fragment were measured over a range of RIIα 1–45 concentrations from 25 to 150 nM (FIG. 1A). Uniform first order binding was recorded with a $K_{assc}$ of $160006 \pm 9700 M^{-1} sec^{-1}$ (n=3) and with a $K_{dis}$ of $0.016 \pm 0.001 M^{-1}$ (n=3) (FIG. 1B). These values were used to calculate a dissociation constant (KD) of 100 nM (n=3) for the RII/gravin fragment interaction (FIG. 1B). The nanomolar binding constant for RII/gravin interaction is well within the physiological concentration range of both proteins inside cells and is consistent with the notion that both proteins may associate in situ.

As demonstrated above, residues fragment 1537–1563 (SEQ ID NO: 2) of gravin form a PKA anchoring site. Of note, this sequence is present in the C-terminus of SSeCKS/ clone 72 (see Example 3). Interestingly, this shared sequence has ten out of fourteen residues which are conserved in the RII-binding region of another mammalian scaffold protein, called AKAP79, which binds PKA, PKC and protein phosphatase 2B [Coghlan et al., 1995b; Klauck et al., 1996]. The identification of a conserved RII-binding sequence in gravin, SSeCKS/clone 72 and AKAP79 is the first example of conserved primary structure in known RII binding regions. This finding was unexpected as it was previously proposed that in spite of a lack of sequence identity among the AKAPs there existed a conservation of secondary structure in the RII-binding motif [Scott et al., 1994]. Therefore, it is likely that gravin, SSeCKS/clone 72 and AKAP 79 are members of a structurally related subfamily of AKAPs which bind more than one kinase or phosphatase.

EXAMPLE 3

Further sequence analysis revealed another potential function of gravin. A search of the nucleotide database using the complete gravin sequence showed that the first 1000 residues are 69% identical to a murine mitogenic regulatory protein SSeCKS [Lin et al., 1995)] also identified in the art as "clone 72", which was recently shown to be a protein kinase C binding-protein and also a protein kinase C substrate. [Chapline et al., 1996].

The ability of gravin to bind PKC was therefore examined. Accordingly, two recombinant gravin polypeptide fragments consisting of amino acids 265–556 (SEQ ID NO: 3) and 1130–1582 (SEQ ID NO: 14) were prepared and overlay analysis similar to the overlay analysis described in Example 2 was performed. The immobilized gravin fragments were incubated with PKC and the bound PKC was detected by using monoclonal antibodies to PKC (Transduction Labs, Lexington, Ky.) [Klauck, et al., (1996)] The 265–556 (SEQ ID NO: 3) fragment was prepared by PCR using primers GACGAGATTGTGGAAATCCAT-GAGG (SEQ ID NO: 19) and GCGCGGATCCAGAGAT-TCTGTAGTTCTGAC (SEQ ID NO: 20). The 1130–1582 (SEQ ID NO: 14) fragment was prepared as described in Example 2. The results showed that PKC bound to the 265–556 fragment (SEQ ID NO: 3), but not to the 1130–1582 fragment (SEQ ID NO: 14). The overlay assay thus showed that the PKC binding fragment of gravin mapped to a region of the sequence between residues 265 to 556 (SEQ ID NO: 3). Neither of the gravin fragments bound PKC in the absence of phosphatidylserine (PS) which is consistent with other reports that phospholipid is a co-factor in the PKC/binding protein complex [Chapline et al., 1996]. It has been suggested that phosphatidylserine (PS) supports a ternary complex of PKC and polybasic regions on the substrate/binding protein [Liao et al., *Biochem.*, 33:1229–1233 (1994)].

Polybasic regions were postulated to participate in formation of a phospholipid bridge between the PKC and its binding proteins [Chapline et al., 1996; Chapline et al., 1993]. In AKAP79, a polybasic region was identified as the PKC binding site [Klauck et al., 1996]. In gravin, there are two polybasic regions in the gravin 265–556 fragment (SEQ ID NO: 3) located between residues 295–316 (FKKFFTQGWAGWRKKTSFRKPK) (SEQ ID NO: 23) and 514–536 (PLKKLFTSTGLKKLSGKKQKGKR) (SEQ ID NO: 24). Both polybasic regions (residues 295–316 and residues 514–536) resemble the PKC-binding site on AKAP79. Synthetic peptides of both polybasic regions of gravin blocked PKC/gravin interactions when assessed by the overlay assay. These experiments show that protein kinase C binds gravin in vitro at one or more polybasic sites located between residues 265–556 of the protein.

The AKAP79 31–52 PKC binding site peptide KASML-CFKRRKKAAKLAKPKAG (SEQ ID NO: 23) blocked PKC binding to gravin. This result demonstrates that both gravin and AKAP79 likely bind to a similar site on PKC.

Figure 2:
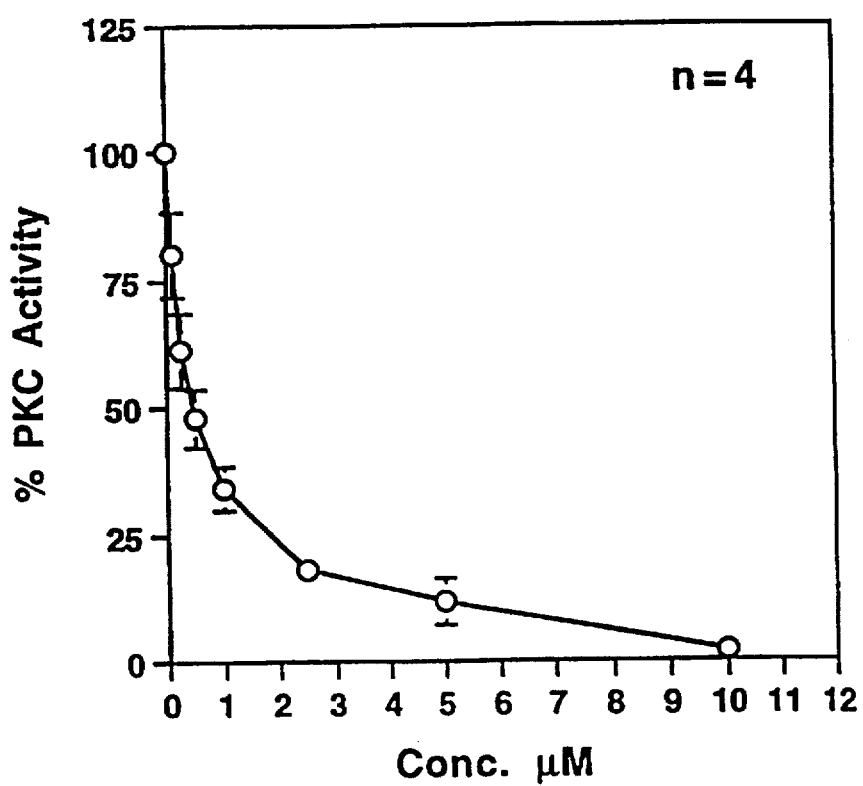
FIG. 2 shows the inhibitory effect of the gravin 265–556 fragment (SEQ ID NO.: 3) on protein kinase C phosphorylation of peptide substrate VRKRTLRRL (SEQ ID NO.: 24) (See example 3).

Further similarity to AKAP79 was demonstrated when the gravin 265–556 (SEQ ID NO: 3) fragment was shown to inhibit PKC activity toward peptide substrate VRKRTLRRL (SEQ ID NO: 24) (Sigma Chemical Co., St. Louis, Mo.) with an $IC_{50}$ of 0.50±0.12 μM (n=4) (FIG. 2). In contrast, the RII binding peptide did not inhibit the kinase. PKC activity was assayed as described [Orr et al., *J. Biol. Chem.*, 269:27715–27718, 1994] in a reaction containing 40 mM HEPES (pH 7.5), 10 mM $MgCl_2$, 0.3 mM $CaCl_2$, 1 mM DTT, 100 μM [$\gamma^{32}P$] adenosine triphosphate (ATP) (500 cpm/pmol), phosphatidylserine (20 μg/ml), and epidermal growth factor receptor peptide (VRKRTLRRL) (SEQ ID NO: 24) as substrate at 30° C. for 10 min. PKC βII (20 ng/μl) was diluted 1:10 in 20 mM Tris (pH 7.9), 1 mg/ml bovine serum albumin (BSA) and 1 mM DTT. Inhibition constants ($IC_{50}$) were determined over an inhibition concentration range of 0.1 to 10 μM gravin 265–556 fragment (SEQ ID NO: 3).

To date, three classes of PKC-binding proteins have been identified by gel overlay and two-hybrid techniques [Faux et al., *Cell*, 85:9–12 (1996a)]. PKC substrate/binding proteins [Chapline et al., 1993] and Receptors for Activated C-kinase (RACKs) [Mochly-Rosen et al., *Proc. Natl. Acad. Sci. USA*, 88:3997–4000, (1991)] have been detected by the gel-overlay procedure, while Proteins that Interact with C-kinase (PICKS), have been isolated in two-hybrid screens [Staudinger et al., 1995]. The data provided herein shows that a region of approximately 290 amino acids supports PKC-binding and fragments corresponding to that region block kinase activity in vitro.

EXAMPLE 4

Monoclonal antibodies are prepared by immunizing Balb/c mice subcutaneously with gravin or gravin fragments in complete Freund's adjuvant (CFA). Subsequent immunizations in CFA or incomplete Freund's adjuvant is performed to increase immune response.

The spleen of the immunized animal is removed aseptically and a single-cell suspension is formed by grinding the spleen between the frosted ends of two glass microscope slides submerged in serum free RPMI 1640, supplemented with 2 mM L-glutamine, 1 mM sodium pyruvate, 100 units/ml penicillin, and 100 μg/ml streptomycin (RPMI) (Gibco, Canada). The cell suspension is filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from naive Balb/c mice are prepared in the same manner.

$2×10^8$ spleen cells are combined with $4×10^7$ NS-1 cells (kept in log phase in RPMI with 11% fetal bovine serum (FBS) for three days prior to fusion), centrifuged and the supernatant is aspirated. The cell pellet is dislodged and 2 ml of 37° C. PEG 1500 (50% in 75 mM HEPES, pH 8.0) (Boehringer Mannheim) is added while stirring over the course of one minute, followed by the addition of 14 ml of serum free RPMI over seven minutes. Additional RPMI can be added and the cells are centrifuged at 200 g for 10 minutes. After discarding the supernatant, the pellet is resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and $1.5×10^6$ thymocytes/ml. The suspension is dispensed into ten 96-well flat bottom tissue culture plates (Corning, United Kingdom) at 200 μl/well. Cells are fed on days 2, 4, and 6 days post-fusion by aspirating 100 μl from each well with an 18 G needle (Becton Dickinson), and adding 100 μl/well plating medium containing 10 U/ml IL-6 and lacking thymocytes.

When cell growth reaches 60–80% confluence (day 8–10), culture supernatants are taken from each well and screened for reactivity to gravin by ELISA. ELISAs are performed as follows. Immulon 4 plates (Dynatech, Cambridge, Mass.) were coated at 4° C. with 50 μl/well with 100 ng/well of p110δ:GST or GST in 50 mM carbonate buffer, pH 9.6. Plates are washed with PBS with 0.05%, Tween 20 (PBST) and blocked 30 minutes at 37° C. with 0.5% Fish Skin Gelatin. Plates are washed as described above and 50 μl culture supernatant is added. After incubation at 37° C. for 30 minutes, 50 μl of horseradish peroxidase conjugated goat anti-mouse IgG(fc) (Jackson ImmunoResearch, West Grove, Pa.) [diluted 1:10,000 in PBST] is added. Plates are incubated at 37° C. for 30 minutes, washed with PBST and 100 μl of substrate, consisting of 1 mg/ml TMB (Sigma) and 0.15 ml/ml 30% $H_2O_2$ in 100 mM Citrate, pH 4.5, is added. The color reaction is stopped with the addition of 50 ml of 15% $H_2SO_4$. $A_{450}$ is read on a plate reader (Dynatech).

Polyclonal antibodies are prepared by immunizing an animal with an antigen comprising a polypeptide of the present invention and collecting antisera from the immunized animal. A variety of animal species including rabbit, chicken, mouse, rat, or guinea pig are useful in preparation of polyclonal antibodies. The 1130–1780 (SEQ ID NO: 17) gravin fragment was used to prepare polyclonal antibodies in rabbit. Rabbit polyclonal antisera R3698 was produced from the 1130–1780 gravin fragment (SEQ ID NO: 17) by a commercial laboratory (Bethyl Labs, Montgomery, Tex.). The 1130–1780 fragment (SEQ ID NO: 17) was made by preparing and expressing a polynucleotide encoding the 1130–1780 fragment (SEQ ID NO: 9) (generated by PCR using the 5' primer, CCGCCATGGTGCATATGTCCGAGTCCAGTGAGC, (SEQ ID NO: 9) and the 3' primer, GGAGGATCCA-GAGATTCTGTAGTTCTG (SEQ ID NO: 13)) as described in Example 2. In addition, the 265–556 fragment (SEQ ID NO: 3) was used to prepare polyclonal antibodies in rabbit and chicken. Rabbit polyclonal antisera, R4310 and chicken polyclonal antisera were produced from the 265–556 fragment (SEQ ID NO: 3) by Bethyl Labs.

EXAMPLE 5

Phorbol ester treatment of a human erythroleukemia cell line (HEL) (HEL 92.1.7, ATCC TIB 180) induces morphological, functional and biochemical changes that are characteristic of macrophage-like cells. One hallmark of this process is the robust induction of gravin [Gordon et al., 1992]. Therefore, the PKA and PKC binding protein profile of HEL cells after prolonged exposure to phorbol esters was examined.

HEL cells were grown in RPMI 1640 containing 12% fetal calf serum and 4 mM glutamine. Gravin expression was induced by culturing with 40 nM phorbol myristate acetate (PMA) for 18 hr. Cell lysates were prepared from either adherent cells grown in the presence of PMA, rinsed with PBS and scraped from the interior of 150 $cm^2$ flasks or from suspension cultures of HEL cells grown in the absence of PMA. Cell pellets were washed twice with PBS prior to resuspension in 20 mM TrisHCl, pH 7.4, 150 mM NaCl, 10 mM EDTA, 0.25% Triton X-100, 0.05% Tween 20, 0.02% $NaN_3$, 10 mM benzamidine, 2 μg/ml pepslatin, 2 μg/ml leupeptin, 4 mM 4-(2-aminoethyl)benzenesulfonyl fluoride hydrochloride (Lysis Buffer) and incubation on ice for 10 min. The extracts were then centrifuged for 10 min at 16,000×g at 4° C. and the cell lysate supernatant was collected. Protein concentrations were measured using the Bio-Rad DC Protein Assay kit.

The extracts from control and treated cells were subjected to western blot analysis with an affinity purified antibody raised against residues 1130 to 1780 of gravin (See Example 4). PMA treatment caused an induction of a 250 kDa protein that specifically reacted with anti-gravin antibodies. Subsequent overlay assays demonstrated that PMA treatment induced the expression of a 250 kDa PKC-binding protein and an RII-binding protein of the same size.

Concomitant with the macrophage-like shift, HEL cells undergoing PMA treatment become adherent and display a considerable cytoplasmic spread [Papayannopoulou et al., Blood, 62:832–845 ( 1983)]. This sometimes results in the formation of actin stress fibers and causes a general flattening of the cell. In order to establish whether gravin aligned with the actin cytoskeleton, phorbol ester treated HEL cells were stained with rhodamine phalloidin as a marker for actin as described below.

HEL cells were grown on glass coverslips in the presence of 40 nM PMA for 18 hr, rinsed with PBS, fixed in 3.7% formaldehyde and extracted in −20° C. absolute acetone. Cells were rehydrated for 1 hr in PBS and 0.2% BSA and then incubated with either affinity purified anti-gravin antibody, R3698, at 0.5 µg/ml or pre-immune IgG at 0.5 µg/ml. After 1 hr the coverslips were carefully washed in PBS and 0.2% BSA and incubated with either a mixture of FITC conjugated donkey anti-rabbit secondary antibody (1:100 dilution, Jackson ImmunoReasearch Laboratories Inc, West Grove, Pa.) and rhodamine conjugated phalloidin (1 unit/coverslip, Molecular Probes, Inc, Eugene, Oreg.) or secondary antibody alone. In situ RII-overlays were performed essentially as described [Coghlan et al., *J. Biol. Chem.*, 269:7658–7665 (1994)]. Prior to incubation with primary antibody, cells were incubated with 80 nM recombinant murine RIIα for 2 hr and unbound RII removed by washing three times in PBS and 0.2% BSA. The immobilized RIIα was detected immunochemically with affinity purified goat anti-murine RII (1 µg/ml) and Texas red conjugated donkey anti-goat IgG secondary (1:100 dilution, Jackson ImmunoReasearch Laboratories Inc, West Grove, Pa.). Control coverslips were treated with the antibody to RII in the absence of exogenous murine RII. Cells were examined using a Leica confocal laser scanning system equipped with a Leitz Fluovert-FU inverted microscope and an argon/krypton laser.

All of the cells displayed a concentration of actin to the periphery. In contrast, gravin staining was predominantly cytoplasmic and only a subset of the cells (approximately 25%) expressed large quantities of the protein. Variable levels of gravin expression were not unexpected as HEL cells represent a heterogeneous population at different stages of differentiation [Papayannopoulou et al., 1983]. Superimposition of images of cells stained for actin and cells stained for gravin showed that both proteins exhibit distinct but partially overlapping subcellular distributions. Control experiments were negative when cells were stained with preimmune serum. More detailed confocal analysis of HEL cells detected gravin staining toward the periphery of the cell and enriched in filopodia at the adherent surface. These findings indicate that gravin functions to enhance HEL cell adhesion to the substratum.

Co-localization of Gravin and PKA

In vitro binding studies described in Examples 2 and 3 indicate that gravin is a kinase scaffold protein. Therefore, co-localization experiments were initiated to determine whether a gravin signaling complex could be detected in HEL cells. Fixed and permeabilized cells pre-treated with PMA were overlayed with recombinant murine RIIα. RII-binding in situ was detected with antibodies that specifically recognize murine RII and mimicked the staining pattern for gravin. Since control experiments confirmed that the anti-murine RII antibodies did not detect the endogenous human RII, the increased RII staining was due to direct association with gravin. This conclusion was supported by additional control experiments showing that in situ RII-binding was blocked by incubation with the Ht 31 anchoring inhibitor peptide.

Finally, the gravin signaling complex was isolated by two complementary biochemical methods: immunoprecipitation and affinity chromatography on cAMP-agarose.

Immunoprecipitation of gravin was performed as follows. HEL cell lysates (200 µl of 15 mg/ml) prepared as described above were incubated with either 15 µg of affinity purified anti-gravin or 15 µg of pre-immune IgG at 4° C. for 18 hr. Immune complexes were isolated by the addition of 200 µl of 10% (v/v) Protein A-Sepharose CL-4B (Sigma, St Louis, Mo.) which had been pre-equilibrated in Lysis Buffer. Following incubation at 4° C. for 90 min the beads were washed once in 0.5M NaCl Lysis Buffer and four times in excess 20 mM TrisHCl, pH 7.4, 150 mM NaCl. The PKA catalytic subunit was released from the immune complex by incubating the Protein-A beads in 200 µl 1 mM cAMP, 20 mM TrisHCl, pH 7.4, 150 nM NaCl for 15 min. The eluate was TCA precipitated prior to analysis on a 4–15% SDS-PAGE gel, electroblotter onto nitrocellulose and the catalytic subunit was detected, as previously described. For the immunoprecipitation and detection of gravin, elution was accomplished by boiling the washed beads in SDS-PAGE sample buffer, separation of proteins on a 4–15% denaturing PAGE gel (5 µg/lane), transfer to nitrocellulose and analysis by gravin western, PKC overlay and RII overlay western [as described above and previously [Klauck et al., 1996].

Gravin was affinity purified by incubating HEL cell lysates (400 µl of 15 mg/ml, prepared as described above with the addition of 10 mM IBMX to the buffer), with 200 µl packed cAMP-agarose (Sigma, St Louis, Mo.) which had been equilibrated in Lysis Buffer with 10 mM IBMX. The slurry was gently mixed for 18 hr at 4° C. and then washed with 1.5 ml Lysis Buffer with 1M NaCl followed by four 1.5 ml washes with 20 mM TrisHCl, pH 7.4, 150 mM NaCl. Elution was accomplished by incubating the beads in 0.5 ml 75 mM cAMP, 20 mM TrisHCl, pH 7.4, 150 mM NaCl for 30 min at room temperature. The final wash and the eluate were TCA precipitated and the entire sample loaded into a single lane on a 4–15% SDS-PAGE gel. The separated proteins were blotted to nitrocellulose and gravin was identified by western analysis as described above.

Immunoprecipitation with gravin antibodies specifically isolated a 250 kDa protein that could be faintly detected when SDS gels were stained with Coomassie Blue. This 250 kDa protein was present only in immunoprecipitates using the affinity purified gravin antibodies and was not detected in control experiments performed with pre-immune serum. Western blot and overlay assays confirmed that the 250 kDa protein was gravin. Moreover, co-precipitation of the PKA holoenzyme was demonstrated by detection of the catalytic subunit in fractions eluted from the immunoprecipitate with cAMP but not in experimental fractions treated with pre-immune serum. The R subunit in the immunoprecipitates was undetectable because the 54 kDa protein migrates with the same mobility as the IgG heavy chain. However, the R subunit/gravin complex was purified from PMA induced HEL cell extracts by affinity chromatography on cAMP-agarose. After extensive washing in high salt buffers, gravin was eluted from the affinity resin with 75 mM cAMP. Since free gravin is refractive to the affinity resin, the protein detected in the eluate was associated with the regulatory subunit. Both co-purification techniques strongly suggest that the PKA holoenzyme is associated with gravin in vivo.

EXAMPLE 6

The nicotinic acetylcholine receptor is a neurotransmitter-gated ion channel comprising five transmembrane polypeptides. The five polypeptides appear to form a transmembrane aqueous pore through which cations can flow. In response to the binding of acetylcholine, the ion channel "opens" and permits the flow of $Na^+$ into the cell (sodium current). The influx of sodium ions causes membrane depolarization which signals the muscle to contract. Individual receptors appear to rapidly open and close during the period of time that acetylcholine remains bound to the receptor. Within a few hundred milliseconds of acetylcholine binding, the channel closes and prevents further flow of sodium current and the acetylcholine signal is terminated.

The sensitivity of the nicotinic acetylcholine receptor to acetylcholine is attenuated by the phosphorylation of the transmembrane polypeptides (desensitization). Prolonged exposure of the receptor to acetylcholine leads to desensitization of the receptor. PKA appears be involved in desensitization of the nicotinic acetylcholine receptor by phosphorylating serine and tyrosine residues of the five transmembrane polypeptides. Myasthenia gravis is an autoimmune disease associated with the development of antibodies to the nicotinic acetylcholine receptors.

The present invention contemplates that gravin functions to localize PKA and PKC to a particular subcellular area of the cell. The role of gravin in coordination of PKA and PKC targeting to cytoskeletal components would be analogous to the role of AKAP79 role in clustering PKA, PKC, and protein phosphatase 2B at the postsynaptic density which is a specialized structure of the dendritic cytoskeleton [Coghlan et al., 1995b; Klauck et al., 1996; Rosenmund et al., Nature, 368:853–856 (1994)].

Modulators which inhibit or abolish binding between gravin and PKA and/or PKC are useful in modulating the localization of PKA and/or PKC to particular subcellular regions. These modulators may include polypeptides which specifically bind to gravin or fragments of gravin which bind to PKA and/or PKC, and other non-peptide compounds (e.g. isolated or synthetic organic or inorganic molecules) which specifically interact with gravin or fragments of gravin.

EXAMPLE 7

The amino acid sequence of gravin exhibits some similarity to SSeCKS/clone 322/clone 72 [Chapline et al., 1996]. There is approximately 69% homology in the first 1,000 amino acids of gravin and SSeCKS. Gravin also exhibits some homology in selected regions to myristoylated alanine rich PKC substrate (MARCKS) [Aderem, Cell, 71:713–716 (1992)]. However, the remainder of each of the protein sequences are distinct. Also, gravin is a protein of 1780 amino acids which migrates with a mobility of 250 kDa on SDS gels, whereas SSeCKS/clone 72 is 1687 residues and migrates at 207 kDa [Lin et al., (1996), Chaplin, et al., (1995) and National Center for Biotechnology Information accession no. 2210332A]. In addition, the identification of five prospective nuclear localization signals has led to the idea that SSeCKS is a nuclear protein [Lin et al., 1995], whereas immunochemical data clearly shows that gravin is cytoplasmic and likely to be a cytoskeletal component. Clone 322 was described as being a tumor suppressor gene which is down regulated in oncogene transformed cells. Based upon a sequence similarities between gravin and clone 72 (and clone 322), gravin may also function as a tumor suppressor gene.

It is well known in the art that cancerous cells are non-adhesive cells. The non-adhesive nature of malignant cancer cells allows these cells to metastasize. The release or de-adhesion of a cancer cell from matrix proteins or other cells is prerequisite to migration or metastasis to new sites. Transformed or tumorigenic cells may be converted to a less tumorigenic state by increased expression of cytoplasmic proteins such as alpha actinin or talin that function in cytoskeletal reorganization, adhesion and migration [Gluck et al., Cell Science, 107:1773–1782 (1994)].

A tissue survey has shown that gravin exhibits a restricted cellular distribution and is predominantly expressed in fibroblasts, neurons and cells derived from the neural crest [Grove et al., 1994]. Since each of these cell types participates in adherent, migratory or path-seeking functions, it was postulated that gravin may regulate membrane/cytoskeleton events [Grove et al., 1994]. This view has been further substantiated by the immunolocalization experiments described in Example 4 which indicates that gravin may concentrate PKA in the ruffles and filopodia of adherent HEL cells. In addition, the data disclosed in Example 4 point toward a role for gravin in cell adhesion. Phorbol ester induced adhesion in HEL cells [Papayannopoulou et al., 1983] is concomitant with the increased gravin expression; whereas loss of an adherent phenotype upon transformation of REF 52 fibroblasts with an SV40 derivative is coincident with the down-regulation of clone 72 [Chapline et al., 1996]. Since phosphorylation events help to maintain the integrity of the membrane/cytoskeleton it is also tempting to speculate that PKA and PKC anchoring by gravin may play a role in adherent processes.

Given that gravin is expressed in adherent cells, but not in non-adherent cells, and given that clone 72 is down-regulated in oncogene transformed cells, gravin is implicated in cancer biology. Similar to its function in localizing kinases near the nicotinic acetylcholine receptor, gravin may also localize one or more kinases near a cell adhesion molecule wherein the response to cellular signals or other stimuli causes the phosphorylation of the cell adhesion molecule. It has been reported that substitution of threonine residues in the cytoplasmic domain of the LFA-1 β subunit abolishes LFA-1 mediated cell adhesion [Hibbs, et al., J. Exp. Med., 174:1227–1238 (1991)]. These threonine residues appear to be phosphorylated during cellular activation [Valmu et al., J. Immunol., 155:1175–1183 (1995)]. These residues are conserved in other integrin β subunits. Thus, phosphorylation may regulate cell adhesion mediated by several distinct integrins.

Modulators which inhibit or abolish binding between gravin and its binding partner are useful in modulating localization of the binding partner by gravin. For example, modulators may interfere with the localization of a kinase near cell adhesion molecules. These modulators may include polypeptides which specifically bind to gravin or fragments of gravin which bind to a gravin binding partner, and other non-peptide compounds (e.g. isolated or synthetic organic or inorganic molecules) which specifically interact with gravin or fragments of gravin.

Numerous modifications and variations in the practice of this invention are expected to occur to those of skill in the art. Consequently, only such limitations as appear in the appended claims should be placed on the invention.

What is claimed:

1. A polypeptide fragment that binds to a type II regulatory subunit of cAMP-dependent protein kinase, said fragment consisting of the amino acid sequence set out in SEQ ID NO.: 1.

2. A polypeptide fragment that binds to a type II regulatory subunit of cAMP-dependent protein kinase, said fragment consisting of the amino acid sequence set out in SEQ ID NO.: 2.

3. A polypeptide fragment of gravin that binds to protein kinase C (PKC), said fragment consisting of the amino acid sequence set out in SEQ ID NO.: 3.

* * * * *